United States Patent
Szoka, Jr. et al.

(10) Patent No.: US 6,897,196 B1
(45) Date of Patent: May 24, 2005

(54) PH SENSITIVE LIPIDS BASED ON ORTHO ESTER LINKERS, COMPOSITION AND METHOD

(75) Inventors: Francis C. Szoka, Jr., San Francisco, CA (US); Xin Guo, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/778,388

(22) Filed: Feb. 7, 2001

(51) Int. Cl.[7] .................. A61K 31/00; A61K 9/127; A01N 43/04
(52) U.S. Cl. .................. 514/1; 514/44; 424/450
(58) Field of Search .................. 424/450, 490, 424/493; 514/1, 44, 2; 435/320.1, 455, 458, 440

(56) References Cited

U.S. PATENT DOCUMENTS

| | | | | |
|---|---|---|---|---|
| 4,897,355 A | * | 1/1990 | Eppstein et al. | 424/450 |
| 5,015,483 A | * | 5/1991 | Haynes et al. | 426/73 |
| 5,395,619 A | * | 3/1995 | Zalipsky et al. | 424/450 |
| 5,447,710 A | * | 9/1995 | Na et al. | 424/9.455 |
| 5,827,533 A | * | 10/1998 | Needham | 424/450 |
| 5,993,850 A | * | 11/1999 | Sankaram et al. | 424/450 |
| 6,008,202 A | * | 12/1999 | Huang et al. | 514/44 |
| 6,028,066 A | * | 2/2000 | Unger | 514/180 |
| 6,106,806 A | * | 8/2000 | Klaveness et al. | |
| 6,132,789 A | * | 10/2000 | Sprott et al. | 426/450 |
| 6,258,351 B1 | * | 7/2001 | Harris | |

OTHER PUBLICATIONS

Guo et al (Bioconj. Chem (2001) 12:291–300).*
(Voet et al, in Biochemistry, Second Edition, John Wiley and Sons, 1995), pp. 280–281.*
Mohr et al (Biochimica et Biophysica Acta, (Jun. 26, 1992) 1126 (3) 247–54).*

* cited by examiner

*Primary Examiner*—Dave T. Nguyen
(74) *Attorney, Agent, or Firm*—Reed Smith LLP; Nathan P. Koenig

(57) ABSTRACT

The invention comprises lipid derivatives that rapidly degrade in the pH range from 4.0 to 7.0 and lipidic delivery systems that contain them. These lipid derivatives can be used to modify the delivery properties of the lipidic delivery systems to enable prolonged circulation times or more rapid drug unloading in the target tissue. The lipid derivatives are amphipathic compounds comprising a hydrophilic head group joined to a hydrophobic group by an acid-labile ortho ester linkage. The delivery systems of the invention exhibit degradation of less than 10% within 3 hours at a pH of 7.4 and degradation greater than 50% within 60 min at a pH of 5.0.

48 Claims, 19 Drawing Sheets

DC-Chol

PH SENSITIVE LIPIDS BASED ON ORTHO ESTER LINKERS, COMPOSITION AND METHOD

BACKGROUND OF THE INVENTION

1. Field of the Invention

The invention relates to drug delivery systems and more particularly to lipidic delivery systems that increase circulation time yet rapidly degrade at reduced pH. The novel lipid derivatives in this invention and the lipidic delivery systems that contain them rapidly degrade in the pH range from 4.0 to 6.0. The lipid derivatives can be used to modify the delivery properties of the lipidic delivery systems to enable prolonged circulation times or more rapid drug unloading in the target tissue.

2. Description of the Related Art

There are a number of important classes of amphipathic molecules that contain both a polar head group and a large hydrophobic moiety. In aqueous phase, such molecules self-assemble into colloidal particles such as liposomes, micelles and hexagonal phase. Liposomes are widely used as models of membrane bilayers and carriers of a variety of diagnostics and medicines. Examples of their use in drug delivery include PEG stabilized liposomes that carry cytotoxic drugs to leaky tumor tissues and cationic liposomes that improve gene transfection.

Ideally, targeted drug delivery systems utilizing liposomes should remain stable until they reach the target site to minimize the premature loss of payload. Upon accumulation at the target site, drug release needs to be at a high enough level for an effective therapeutic response. Since the decrease of pH is implicated in many physiological and pathological progressions such as endosome processing, tumor growth, inflammation and myocardial ischemia, it has been extensively exploited to trigger the release of drugs from liposomal delivery systems in the past twenty years. Most of the reported pH sensitive liposomes are based on the neutralization of excess negative charges on their surface upon protonation, which reduces the hydrodynamic diameter of lipid head groups and triggers the change of lipid bilayers to hexagonal phases. However, at neutral pH, these excess negative charges induce undesired interactions with serum proteins and fixed macrophages, leading to rapid elimination of the liposomes from circulation. Efforts to circumvent this difficulty and provide a non-ionic pH sensitive lipid have employed a neutral monosaccharide as the head group, which is attached to long hydrophobic chains via an acetal moiety. However, these acetal analogs hydrolyze relatively slowly at pHs 5 to 7 as found in physiological environment and need a pH less than 4 for rapid degradation. Recently, a number of acid- and light-sensitive lipids containing vinyl ether moieties have been reported. Neverthelss, the rate of hydrolysis at pH 5 of these vinyl esters is not optimal for rapid drug release.

The pH-sensitive properties of the diortho ester moiety have been used by the prior art to develop sustained drug release systems. These systems rely on polymer chains of multiple ortho esters that degrade in multiple places.

Methods to enhance the circulation time by coating the liposome with polyethyleneglycol have been devised. This PEG coating works to extend the circulation time by shielding the liposome surface so that the liposomes do not appreciably interact with cells that remove liposomes from circulation. However, once the PEG-coated liposomes reach the target organ they do not interact with cells in this organ.

The efficiency of delivery remains as a key factor for the success of gene therapy. Cationic liposomes are the most intensively studied synthetic gene vectors with substantial success in vivo. However, most of the cationic lipoplexes are trapped in the endosomes following cellular uptake and finally processed to lysosomes, where they are degraded. In fact, viruses which infect their host cells via the endocytic pathway rely on specific proteins to destabilize endosome membranes so as to translocate the viral genomic DNA into the cytoplasm.

Thus, what has been needed is a delivery system that release its encapsulated material at a mildly acidic pH encountered in physiological or pathological scenario. There is a further need for compositions and drug delivery systems that lengthen circulation time while still providing effective release. An additional need is a drug delivery system optimized for receptor-mediated uptake. This invention satisfies these and other needs.

SUMMARY OF THE INVENTION

The invention is a lipidic ortho ester conjugates (LOC) comprising a hydrophilic head group portion, a hydrophobic portion and an ortho ester-based, acid-labile linker, capable of imparting pH-sensitivity to an encapsulator, wherein the linker hydrolyzes at an increasing rate as the pH is reduced below 7. Preferably, the hydrophilic portion comprises a group such as a polyethyleneglycol, polyglycerol, hydroxylated dendrons, poly(methyloxazoline), poly(ethyloxazoline) and polyvinylpyrrolidone or suitable anionic groups, primary amines, secondary amines, tertiary amines, quaternary ammoniums or imidazoles or other suitable cationic groups and targeting ligands. More preferably, the hydrophilic head group comprises a polymer capable of increasing the circulation time of an encapsulator in animals such as methoxypolyethylene glycol. The hydrophobic portion comprises a group such as diacyl glycerols, distearoylglycerol, dipalmitoylglycerol, dimyristoyl glycerol, dioleoyl glycerol, or other diacyl/steryl hydrophobic groups, tocopherol, cholesterol, coenzyme Q, and ceramide. The LOC is an amphipathic low-pH sensitive compound. The ortho ester linker may comprise a double ortho ester such as a diketene acetal deriviative, for example, 3,9-dialkoxylated 3,9-Diethyl-2,4,8,10-tetraoxaspiro[5,5] undecane derivatives, or a single ortho ester such as a dichloromethylmethyl ether derivative.

In a preferred embodiment, the LOC comprises a pH sensitive lipid. The lipid may be combined with conventional lipids to form inventive biologic encapsulators such as liposomes, emulsions, micelles and other lipidic bodies. Examples of suitable lipids include phosphatidylcholine, phosphatidylglycerol, phosphatidylethanolamine, phosphatidylserine, phosphatidic acid, cholesteryl hemisuccinate, cholesterol sulfate, ceramide, cardiolipid, N[1-,2dioleoyl-3-trimethyl]ammonium propane (DOTAP), dimethyldioctadecylammonium bromide (DDAB), 1-palmitoyl-2-oleoyl-sn-glycero-3-ethyl-phosphocholine,N [1-(2,3-dioleyloxy)propyl]-N,N,$N_1$-triethylammonium (DOTMA), triglycerides, squalene, coenzyme Q and alkyl acylcarnitine esters. Alternatively, the encapsulator may comprise entirely the pH sensitive lipid. As such, the LOCs of the invention can be used to create stable encapsulators at neutral pH's that destabilize at reduced pH's. Preferably, the encapsulators comprising the LOCs exhibit a degradation of less than 10% over 3 hours at a pH of 7.4 and a degradation of greater than 50% within 60 min at a pH of 5.0. Due to the improved sensitivity towards small decrease in pH, the compositions of this invention may be used in drug delivery, diagnostics, biosensors or analytical devices, and the like.

Specific LOCs of the invention include PEG-diortho ester-distearoyl glycerol conjugates, cationic lipidic derivatives of dichloromethylmethylether, LOCs comprising targeting ligands, and others. Encapsulators embodying features of the invention include LOCs and DOPE, such as POD/DOPE or DOC/DOPE, LOCs and fusogenic PE encapsulators, LOCs and targeting ligand encapsulators, and others.

Methods of the invention comprise delivering a drug to a cell by administering an encapsulator comprising an LOC and the drug. The delivery can be in vitro or in vivo. The methods also comprise introducing an LOC to an encapsulator. The LOC can be formulated as a micelle dispersion, an emulsion, a dry film, or any other suitable composition.

The inventive ortho ester conjugates comprising a cationic head group and a cone-shaped lipidic alcohol can be used for the generation of cationic lipoplexes with an improved endosome-disrupting, and hence gene-transfering effect. At neutral pH, liposomes composed of the cationic conjugate and a fusogenic helper lipid condense spontaneously with DNA into lipoplexes; upon endocytosis and acidification of the endosomes, the conjugate is hydrolyzed to expose the conical lipidic alcohol and the fusogenic helper lipid. These lipids in turn disrupt endosomal membranes and release the initially complexed DNA into the cytoplasm.

BRIEF DESCRIPTION OF THE DRAWINGS

The aforementioned advantages of the invention, as well as additional advantages thereof, will be more fully understood from a detailed description of a preferred embodiment when taken in conjunction with the accompanying drawings in which.

DETAILED DESCRIPTION OF THE INVENTION

Abreviations and Definitions

ANTS, 8-aminonaphthalene-1,2,3-trisulfonic acid; BPE, p-hydroxybenzamidine phosphatidylethanolamine; CHEMS, cholesteryl hemisuccinate; Chol, cholesterol; DCChol, a pH-insensitive cationic lipid; DOC, dimethylethanolamine-ortho ester-cholesterol, the tertiary amine conjugate; DOPE, dioleoylphosphatidylethanolamine; DPX, p-xylenebis(pyridinium) bromide; DSG, 1,2-distearoyl glycerol; DSPE-PEG, 1,2-distearoyl-sn-glycero-3-phosphoethanolamine-N-[poly(ethylene glycol)-2000; HEPES, (hydroxyethyl)piperazine-N-2-ethanesulfonic acid; PEG, polyethylene glycol; POD, methoxypolyethylene glycol 2000-diortho ester-distearoyl glycerol conjugate; POPC, 1-palmitoyl-2-oleoylphosphatidylcholine; POPG, 1-palmitoyl-2-oleoylphosphatidylglycerol sodium salt; S.D., standard deviation; TLC, thin layer chromatography.

As used herein, the terms amphipathic low-pH sensitive compound and lipidic ortho ester conjugates refer to the inventive compositions of the method, generally comprising a hydrophilic portion, a hydrophobic portion and an acid-labile ortho ester linker, capable of imparting pH sensitivity to an encapsulator under biological scenarios. The hydrophilic portion generally comprises any moiety that interacts with water and may be anionic, cationic or non-ionic. The term encapsulator refers to micro- or nano-particulate systems that contain another compound and may be used to deliver that compound in a biological system. Encapsulators include liposomes, emulsions, micelles and other lipidic bodies. The compound may be contained as with a liposome or embeded as with micelles or emulsions. Drug refers to any compound having biological activity or other therapeutic or diagnostic utilty. The hydrophilic portion can also be called the head group. The hydrophobic portion can also be called the tail. The LOC can also be called: ortho ester conjugate, conjugate. The Hydrophilic alcohol refers to an alcohol used as the synthetic Intermediate to build the hydrophilic portion of the LOC. Hydrophobic alcohol refers to an alcohol used as the synthetic Intermediate to build the hydrophobic portion of the LOC. Linker or linker group refers to the chemical group that connects the hydrophilic portion and the hydrophobic portion of the LOC. Linker molecule refers to the synthetic Intermediate to build the linker of the LOC.

EXAMPLE 1

Figure 1:
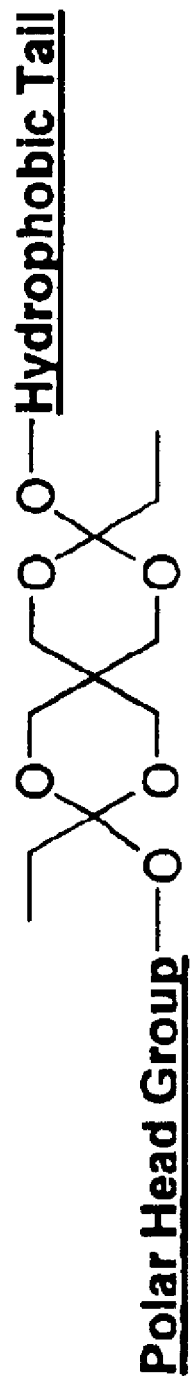
FIG. 1 illustrates the general structure of the diortho ester conjugates used in the invention.
Figure 2:
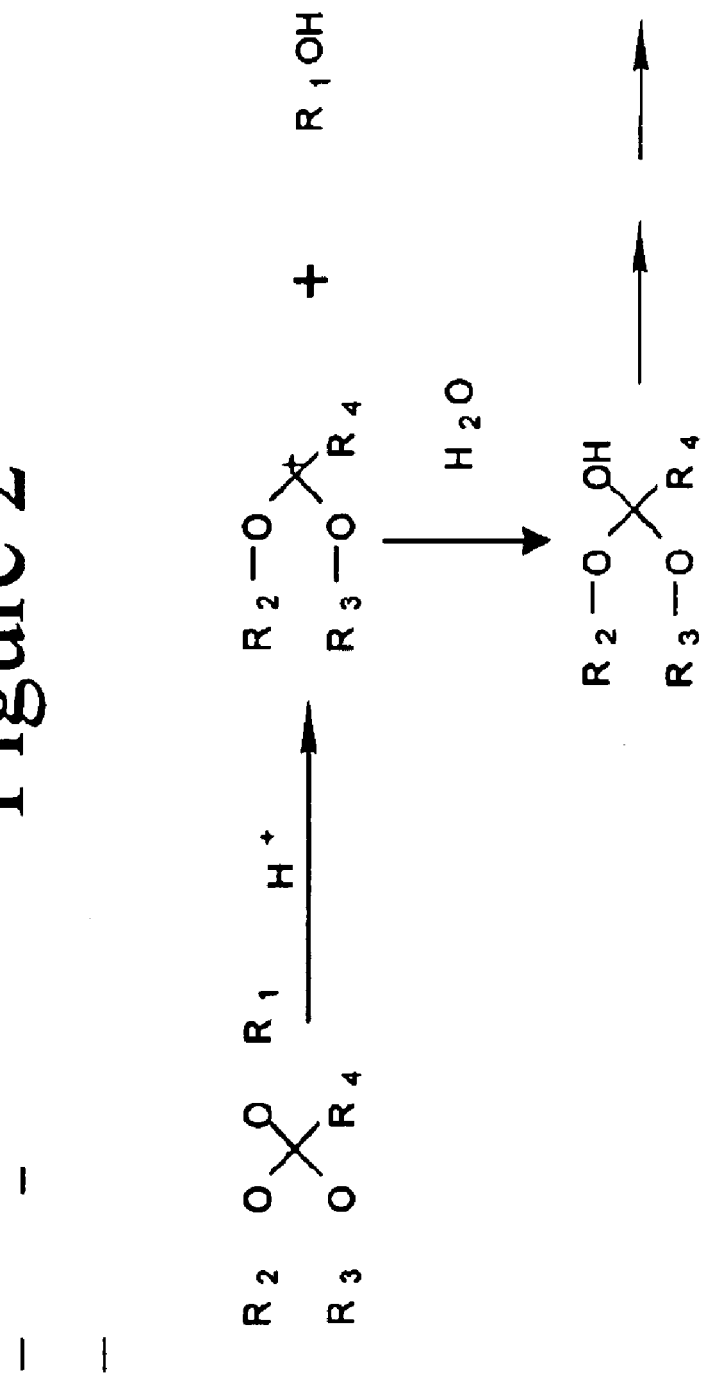
FIG. 2 shows a generalized mechanism of ortho ester hydrolysis.

One embodiment of the invention comprises biocompatible liposomes, which are sensitive to small pH decrease. Preferably, these comprise a novel class of lipids that possess an acid labile diortho ester linker between the hydrophilic head group and the hydrophobic tail as shown in FIG. 1. In this embodiment, a variety of head groups and tails can be conjugated together to render pH sensitive lipids of different properties. Ortho esters are relatively stable under basic and neutral conditions but hydrolyze quickly at acidic pH due to a stabilized dialkoxy carbocation intermediate as shown in FIG. 2.

Figure 3:
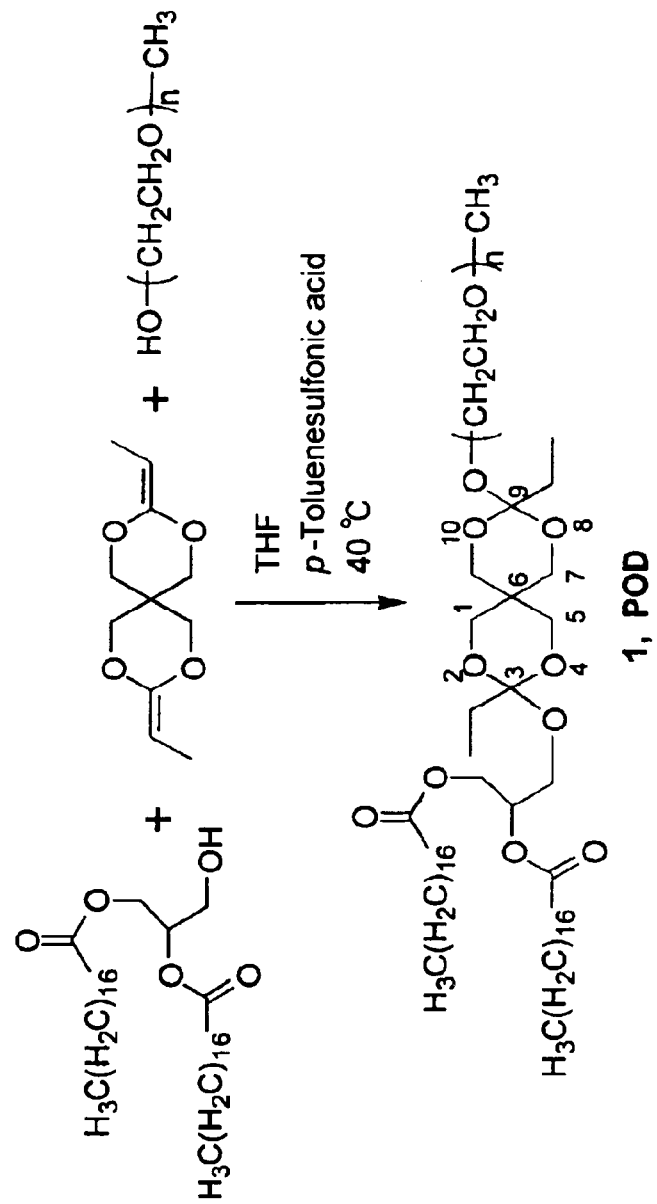
FIG. 3 shows the synthesis of the inventive methoxyPEG-diortho ester-distearoyl glycerol conjugate.

An example of the LOCs of the invention is the novel lipid (POD) that comprises a PEG head group, a diortho ester linker and a distearoyl glycerol hydrophobic tail. The synthesis of POD is shown in FIG. 3. POD can be used to prepare long circulating and acid-triggerable liposomes in combination with DOPE, a lipid that by itself does not form stable liposomes but hexagonal phases at neutral pH. This embodiment comprises a lipid that degrades specifically in a low-pH environment but is inert under neutral physiological conditions. PEG was chosen as the head group since it is one of the most stable synthetic polymers in vivo and liposomes coated by PEG have a prolonged circulation period. The monomethyl ether of PEG-2000 was used for synthesis to preclude cross-linking or polymerization. The 3,9-diethyl-2,4,8,10-tetraoxaspiro[5,5]undecane moiety was chosen as the diortho ester linker, based on its pH sensitivity and biocompatibility in polymeric drug delivery systems. Distearoyl glycerol, with two saturated hydrocarbon side chains, is attached to the diortho ester linker as the hydrophobic tail to anchor the conjugate into lipid bilayers. If the conjugate is incorporated into liposomes of unsaturated phosphatidylethanolamine, distearoyl glycerol would be regenerated in the bilayers upon hydrolysis, and would favor the formation of hexagonal phases due to its conical structure.

The ortho ester linker can comprise a diortho ester, such as a diketene acetal. For example, 3,9-diethylidene-2,4,8, 10-tetraoxaspiro[5,5]undecane can be synthesized by methods known in the prior art.

Monomethyl ether of PEG (MW 2,000) can be obtained from Shearwater Polymers, Inc (Huntsville, Ala.). Distearoyl glycerol can be obtained from Genzyme (Cambridge, Mass.). Triethylamine can be obtained from Aldrich (Milwaukee, Wis.) and redistilled under Ar before use. 1-Palmitoyl-2-oleoylphosphatidylcholine (POPC), 1-palmitoyl-2-oleoylphosphatidylglycerol sodium salt (POPG), dioleoylphosphatidylethanolamine (DOPE) and 1,2-distearoyl-sn-glycero-3-phosphoethanolamine-N-[poly (ethylene glycol)-2000 (DSPE-PEG) can be obtained from Avanti Polar Lipids (Birmingham, Ala.). Cholesteryl hemisuccinate (CHEMS) can be obtained from Sigma (St. Louis, Mo.). 8-Aminonaphthalene-1,2,3-trisulfonic acid (ANTS) and p-Xylenebis(pyridinium) bromide (DPX) can be obtained from Molecular Probes, Inc. (Junction City, Oreg.). MilliQ water, which had a pH of approximately 8 when freshly prepared, was used to prepare all the aqueous buffers. All other chemical reagents and solvents were purchased from Aldrich or Fisher. Ratios of components in chromatography solvent systems are in volume unless stated otherwise. Ratios of lipid components in liposomes are in mole units.

$^1$H-NMR spectra were recorded on an Oxford AS 400. Electrospray mass spectra (ESMS) were recorded on a Sciex (PE, Foster City, Calif.) at the Mass Spectrometry Facilities, University of California at San Francisco. Fourier transformed infrared spectra were measured with a Nicolet Impact 400. The FT-IR samples were applied as a $CHCl_3$ solution onto the surface of a NaCl crystal, dried under Ar, and subsequently measured. Elemental analysis was carried out by Microanalytical Lab at College of Chemistry, University of California at Berkeley.

Synthesis of 3,9-Diethyl-3-(2,3-distearoyloxypropyloxy)-9-(methoxypolyethyleneglycol2000-1-yl)-2,4,8,10-tetraoxaspiro[5,5]undecane One gram of PEG (2000) monomethyl ether (0.5 mmol) and 312.5 mg of distearoyl glycerol (0.5 mmol) were dissolved in 5 mL of anhydrous THF under Ar. A heat gun was used to melt 3,9-diethylidene-2,4,8,10-tetraoxaspiro[5, 5]undecane and 100 μL (110 mg, 0.5 mmol, d=1.1) of the melted compound was taken by a dry syringe and injected into the THF solution. One drop (~40 μL) of 0.6 mg/mL p-toluenesulfonic acid in anhydrous THF was added and the reaction mixture was stirred at 40° C. under Ar for 2 hours. The reaction was stopped by adding 200 μL triethylamine followed by quenching the reaction into 30-fold volume excess of 1% triethylamine in methanol. Four grams of silica gel were added to the solution and the mixture was evaporated under reduced pressure. The residue was poured onto a silica gel column (45 grams) equilibrated with the eluting solvent system (triethylamine/chloroform=1/50). The column was eluted and fractions corresponding to the product were pooled, evaporated, and dried in high vacuum to give 275 mg (20%) purified product. TLC $R_f$ 0.4 in $CHCl_3$/ MeOH/30% w/w $NH_4OH$ (100:15:1); FTIR 2910 $cm^{-1}$ ($CH_2$ and $CH_3$), 2850 $cm^{-1}$ ($CH_2$ and $CH_3$), 1743 $cm^{-1}$ (Ester C=O), 1109 $cm^{-1}$ (PEG and ortho ester C—O); $^1$H NMR (400 MHz, $CDCl_3$, chemical shifts relative to TMS signal): 5.22 (1H, m, glycerol methine), 3.7–4.2 (4H, m, glycerol methylene), 3.0–3.7 (~170H, m, $OCH_2$ and $OCH_3$), 2.2–2.4 (4H, m, $CH_2COO$), 1.65–1.76 (4H, m, $CH_2CH_2COO$), 1.54–1.65 (4H, m, $CH_2CH_3$ on Spiro rings), 1.04–1.36 (56H, m, $CH_3(CH_2)_{14}CH_2CH_2COO$), 0.82–0.97 (12H, m, $CH_2CH_3$); ESMS, calcd for $[M+Na]^+$ with 36-48 $CH_2CH_2O$ units from methoxyPEG: $C_{123}H_{240}O_{46}Na$ 2476.6, $C_{125}H_{244}O_{47}Na$ 2520.7, $C_{127}H_{248}O_{48}Na$ 2564.7, $C_{129}H_{252}O_{49}Na$ 2608.7, $C_{131}H_{256}O_{50}Na$ 2652.7, $C_{133}H_{260}O_{51}$ Na 2696.8, $C_{135}H_{264}O_{52}Na$ 2740.8, $C_{137}H_{268}O_{53}Na$ 2784.8, $C_{139}H_{272}O_{54}Na$ 2828.8, $C_{141}H_{276}O_{55}Na$ 2872.9, $C_{143}H_{280}O_{56}Na$ 2916.9, $C_{145}H_{284}O_{57}Na$ 2960.9, $C_{147}H_{288}O_{58}Na$ 3004.9, found 2478.3 (33%), 2521.1 (47%), 2565.3 (62%), 2609.3 (77%), 2654.2 (94%), 2697.3 (100%), 2741.4 (98%), 2785.3 (93%), 2830.4 (85%), 2874.4 (60%), 2917.5 (46%), 2962.4 (37%), 3006.4 (26%). Anal. Cald. for ($C_{135}H_{264}O_{52}$, C 59.62, H 9.78; $HC_{137}H_{268}O_{53}$, C 59.54, H 9.77; $C_{139}H_{272}O_{54}$, C 59.46, H 9.76; $C_{141}H_{276}O_{55}$, C 59.39, H 9.76; $C_{143}H_{280}O_{56}$, C 59.31, H 9.75; $C_{145}H_{284}O_{57}$, C 59.24, H 9.74; $C_{147}H_{288}O_{58}$, C 59.17, H 9.73) found C 59.16, H 9.57, N<0.2.

It should be noted that POD is actually a mixture of conjugates with the methoxyPEG head group comprising of a narrow distribution of molecular weights around 2000, due to the polydisperse nature of the commercially available PEG2000 monomethyl ether. The electrospray mass spectrometry showed a distribution of peaks centered on 2697 dalton, corresponding to mono-sodiumated molecular cations with different numbers of ethylene glycol units. The heterogeneity of PEG as well as the stereochemistry of the conjugate also resulted in NMR peaks of POD appearing as multiplets, a feature which is known in the art. Alternatively, methoxyPEG can be used having an average molecular weight from about 200 to 20000 to provide the LOC with differing properties as desired.

Acid Sensitivity of POD as Monitored by Thin Layer Chromatography

Conical polystyrene microcentrifuge tubes (0.5 mL) containing 20 μL 100 mM sodium phosphate buffer of different pH were pre-warmed at 37° C. for 30 min and silica gel TLC plates (WhatmanCE from Whatman Ltd, Maidstoned, Kent, England) were pre-equilibrated with the solvent system ($CHCl_3$/MeOH/$NH_4OH$=100:15:1) by running the plates without samples followed by brief air-drying. Eight milligrams of POD was dissolved into 100 μL water by vortexing and 20 μL of the solution was added into each of the pre-warmed tubes and mixed thoroughly. The tubes were incubated at 37° C. and 10 μL of the solutions were aliquoted at different time points and mixed with 10 μL of 10% concentrated $NH_4OH$ (30% w/w) in acetone to stop the hydrolysis. Five microliters of the mixture was spotted onto pre-equilibrated TLC plates. Three microliters of distearoyl glycerol, monomethyl ether of PEG2000 and POD in 10 mg1 mL CHCl$_3$ solution were also spotted as standards. TLC plates were developed, heated at 150° C. for 5 min and stained in I$_2$ chamber for 1 h to observe the locations of POD and its degradation products.

Figure 6:
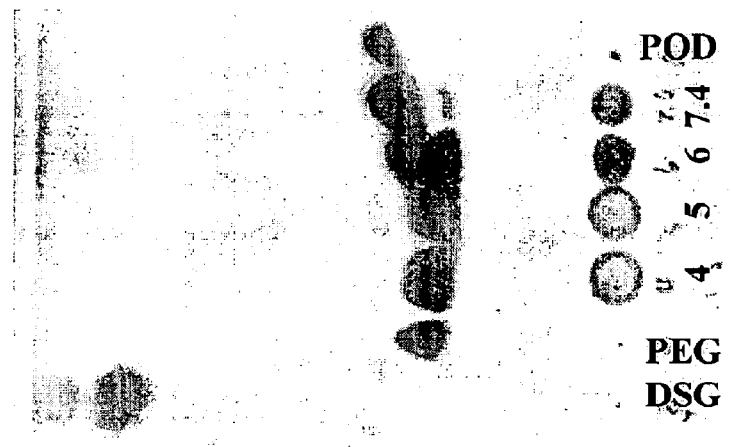
FIGS. 4–6 shows TLC monitored degradation of the inventive POD over time at varying pH.
Figure 5:
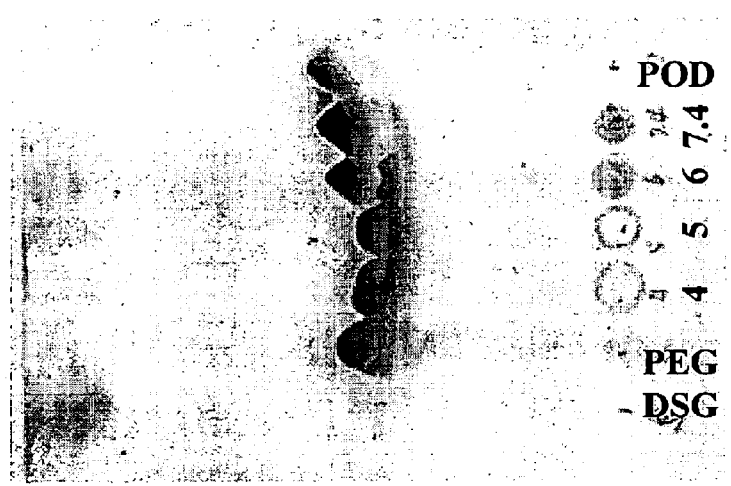
Figure 4:
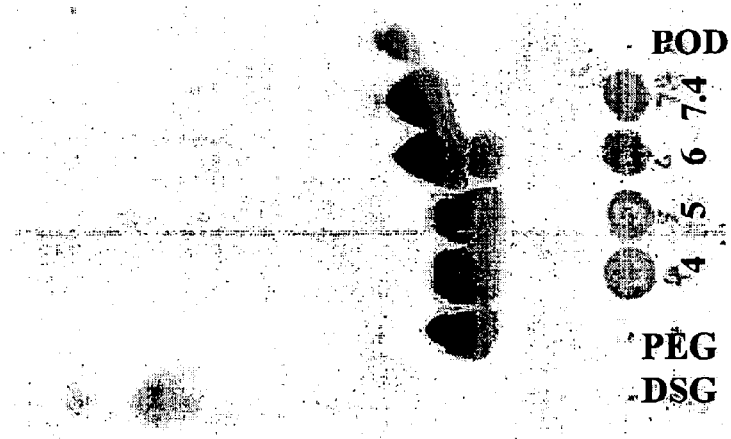

As shown in FIGS. 4–6, within one hour of incubation at 37° C., POD was completely degraded in buffers of pH 4 and 5 as indicated by the disappearance of the compound spot at Rf~0.4. However, in the buffer of neutral pH 7.4, most of the conjugate remained intact over 3 hours. In the buffer of pH 6, POD degraded with an approximate half-life of 2.5 hours. Lipids were incubated for the period of 1 h (FIG. 4), 2 h (FIG. 5) and 3 h (FIG. 6) in Na$_2$HPO$_4$ buffers of the specified pH. POD, methoxyPEG and DSG in CHCl$_3$ solution were spotted alongside as standards.

As expected from the acid-catalyzed hydrolysis shown in Figure, the degradation of POD yielded both more hydrophilic (Rf~0.3) and more hydrophobic (Rf~0.8) materials, presumably derivatives of methoxyPEG and distearoyl glycerol, respectively. The hydrophilic degradation products gave more intensely stained spots than the hydrophobic derivatives, because PEG derivatives are much more sensitive to iodine staining then are the saturated acyl chains. Similar results can be obtained when the TLC plates are stained with Molybdate reagent, which also clearly shows the hydrophobic degradation products.

POD showed a remarkably quick degradation even at a mildly acidic pH of 5 to 6. Such sensitivity to acidic pH is significantly higher than that of acetals, vinyl ethers and polyortho esters. The higher sensitivity of POD may be attributed to the following two factors. First, the dialkoxy carbocation intermediate of ortho ester hydrolysis has four lone pairs of electrons over which to distribute the positive charge from the carbon, and hence is much more stable, see FIG. 2, than the monoalkoxy carbocation intermediate, stablized by two lone pairs of electrons, in the case of acetals and vinyl ethers. Secondly, the methoxyPEG head group of POD is more hydrophilic than the functional groups of the reported polyortho esters, allowing better hydration and faster proton transfer to the diortho ester linkage. When POD was incorporated into liposomes composed of a high percentage of DOPE, POD hydrolysis at pH 5 to 6 triggered the extensive aggregation and leakage of the liposomes in 10 to 100 minutes.

The rapid hydrolysis of POD at mildly acidic pH is a very useful property for drug/gene delivery systems because the decrease of pH at potential therapeutic sites may be only one pH unit or less. For example, the transit through the endosomes in cells occurs in about 10 to 30 minutes with pH in the range of 5 to 6 before the endosomal contents are delivered into the lysosome. Therefore, it is important for pH sensitive liposomes to respond quickly to the initial drop in pH and release their contents prior to trafficking into the lysosomal compartment. The pH-dependent release profile of POD/DOPE liposomes may also be important for triggered release at inflammatory tissues and solid tumors, where the pH is only 0.5 to 1 unit more acidic than that of the circulation.

Liposome Formation

Reverse-phase vesicles (REV) were prepared as as known in the art in 50 mM ANTS, 50 mM DPX and 5 mM HEPES at pH 8.5. The vesicles were extruded 5 times through a 0.2-μm polycarbonate membrane (Nucleopore Corp., Pleasanton, Calif.) through a hand held extrusion device (Avestin, Ottawa, Ontario, Canada). A Sephadex G-75 column was used to separate vesicles from unencapsulated material with an elution buffer composed of 5 mM HEPES and 145 mM NaCl, pH 8.5. All freshly prepared liposomes had mean diameters ranging from about 180 to 200 nm (cumulant results) and a polydispersity index of less than 0.2 as measured by a Malvern Zeta1000 Dynamic Light Scattering Instrument using the PCS 1.32a software. The encapsulated volume was 0.25–0.3 μL/μmol total lipid. Lipid concentrations were determined based on lipid phosphorus as known in the art.

The incorporation of POD into a high percentage of DOPE, a fusogenic lipid, stabilizes a lamellar structure in neutral and alkaline solutions, and yet induces destabilizing phase changes upon cleavage of its methoxyPEG head group by hydrolysis at low-pH. ANTS and DPX were encapsulated into liposomes by reverse phase evaporation and their leakage from the vesicles were used to monitor pH triggered release of liposomal contents. Liposomes of defined size were prepared by extruding 5 times through polycarbonate membranes of 200 nm pore diameter. Unencapsulated ANTS/DPX was then removed by size exclusion chromatography. Liposomes composed of 10% POD and 90% DOPE were readily prepared and remained stable for up to two weeks in HBS buffer at pH 8.5 (5 mM HEPES, 145 mM NaCl) at 4° C. with no significant increase in particle size or in residual ANTS fluorescence. Different ratios of POD to DOPE are also suitable. Generally, the POD to DOPE ratio can range from about 3:97 to 15:85.

Acid Triggered Liposome Aggregation

Conical polystyrene microcentrifuge tubes (0.5 mL) containing 300 μL of buffers of various pH (50 mM NaOAc/HOAc and 100 mM NaCl for pH<6; 50 mM NaH$_2$PO$_4$/Na$_2$HPO$_4$ and 100 mM NaCl for pH 6 and above) were incubated at 37° C. for 30 min. The liposome preparation was warmed to room temperature and an aliquot (100 μL) was added to each tube and mixed thoroughly. The tubes were incubated at 37° C. for different time periods and 30–40 μL of the mixtures were aliquoted and transferred into disposable polystyrene fluorimeter cuvettes containing 1.5 mL 100 mM NaHCO$_3$/50 mM NaCl buffer at pH 9. The samples were mixed by gently inverting the cuvettes 2 to 3 times.

Photon Correlation Spectrometry of the samples was then measured with a Malvern apparatus (Zeta 1000) to determine the size distribution of the liposomes. Typically, three measurements of 2–5 min were made for each sample, using the automatic algorithm mode for data analysis. The average of the three cumulant results of each sample that agreed to within 10% was used.

When pH sensitive liposomes composed of phosphatidylethanolamine (PE) are subjected to low-pH, the PE lipids undergo a contact-induced aggregation and a phase transition from the lamellar to the hexagonal phase. PEG lipids at a high enough concentration on the liposome surface can shield the PE lipids of one liposome from contacting those of another liposome, thus preventing aggregation and membrane-destabilizing phase changes. Thus one can follow the loss of the methoxyPEG coating from the liposome surface as a result of POD hydrolysis by monitoring the aggregation of POD/DOPE liposomes at different pH with Photon Correlation Spectroscopy (PCS). However, as indicated by the TLC assays, the kinetics of the aggregation, particularly at pH below 5.5, may be too fast to be monitored by PCS, which takes about 10 to 20 min for a triplicate measurement. In order to circumvent this problem, the aggregation process may be "frozen" by quenching aliquots of samples in excess buffer of pH 9. The quenching stopped the acid-catalyzed POD hydrolysis and prevented the liposomes/lipid particles from contacting each other by inducing negative charges to their surfaces via deprotonation of the amine in DOPE. Such "base-freezing" prevents size increases in the aggregation products. Further, quenching of the reaction to pH 9 does not result in dispersion of aggregates into smaller particles. This was confirmed by taking aliquots of liposomes incubated at pH 6 and diluting them in the same pH 6 buffer. The particle size of the liposomes was then immediately determined by a single PCS measurement of two minutes. The size data thus obtained were not significantly different from the diameters measured after "base-freezing". Furthermore, the samples quenched at pH 9 gave the same PCS readings after being left overnight at room temperature. Thus the base quenching yielded a reproducible value that reflected the particle size distribution at the quench time. Therefore, the light scattering of the aliquots quenched at pH 9 were recorded and the particle diameter from the cumulant results was plotted against incubation time in FIG. 7. Varying pH from 4 to 7.5 was used as follows: (A) pH 4; (B) pH 4.5; (C) pH 5; (D) pH 5.5; (E) pH 6.2; (F) pH 7.5.

Figure 7:
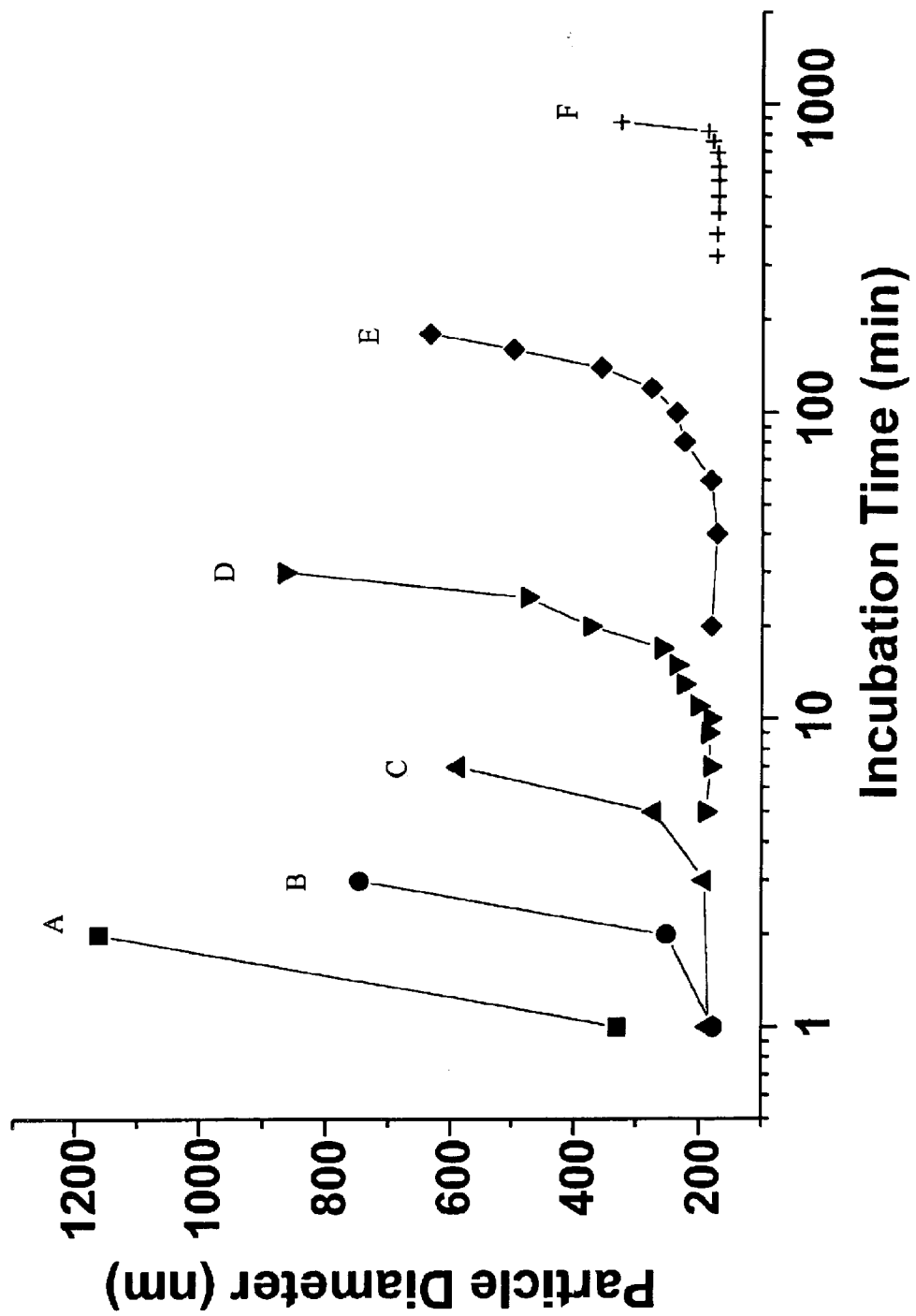
FIG. 7 illustrates the aggregation of POD/DOPE liposomes in buffers of different pH.

The aggregation process showed a pH dependent lag phase followed by a rapid increase in diameter (FIG. 7). At pH 7.4, the POD/DOPE liposomes were relatively stable and the aggregation did not occur after more than 10 hours of incubation at 37° C. In buffers of lower pH, the lag phase was much shorter. At pH 6, the liposome size started to increase after 1 hour and when the pH was decreased 4;6 to 5, extensive aggregation was observed within 10 min. Thus, the kinetics of the liposome aggregation correlated with that of pH-dependent POD degradation shown by the TLC studies. These results demonstrate the ability of POD to protect the DOPE-containing liposomes from aggregating and converting into hexagonal phases until the methoxyPEG head groups are removed from the surface of the liposomes at low pH.

Acid Triggered Content Leakage by ANTS/DPX Assay

The ANTS/DPX assay was used to monitor leakage of ANTS from liposomes.

Fluorescence measurements were made on a Spex Fluorolog photon counting instrument (Edison, N.J.) using a 150-W xenon light source. Excitation was at 370 nm (1.25 mm slit). The 90° emission signal at 550 nm (5 mm, 5 mm slits) resulting from the dequenching of ANTS released out of liposomes was observed through a Corning 3–68 nm cutoff filter (>530 nm). The raw fluorescent data were converted into ASCII data files and processed mathematically by Microsoft Excel. The residual fluorescence of the liposomes at the starting time ($t_0$) of leakage experiments, $F_0$, was set as 0% release. At the end of each leakage experiment the liposomes were lysed with the detergent dodecyloctaethylene glycol monoether ($C_{12}E_8$) and the maximal fluorescence thus obtained, $F_{100}$, was taken as 100% release. The leakage of ANTS at a particular time point was then determined by the formula: Percentage of Leakage=$(F_t-F_0)/(F_{100}-F_0) \times 100$, where $F_t$ corresponds to the fluorescence intensity observed at the time point.

In leakage experiments of POD/DOPE liposomes in aqueous buffers of different pHs, the assays were started by injecting small volumes (5–10 µL, using a Hamilton syringe) of concentrated liposome suspensions into a magnetically stirred quartz cuvette containing 2 mL of the buffer (50 mM NaOAc/HOAc and 100 mM NaCl, pH<6; 50 mM $NaH_2PO_4/Na_2HPO_4$ and 100 mM NaCl, pH 6 and above) at 37° C. The starting time, $t_0$ was set 5 to 10 seconds after the injection when the fluorescence signal first became stable.

Figure 8:
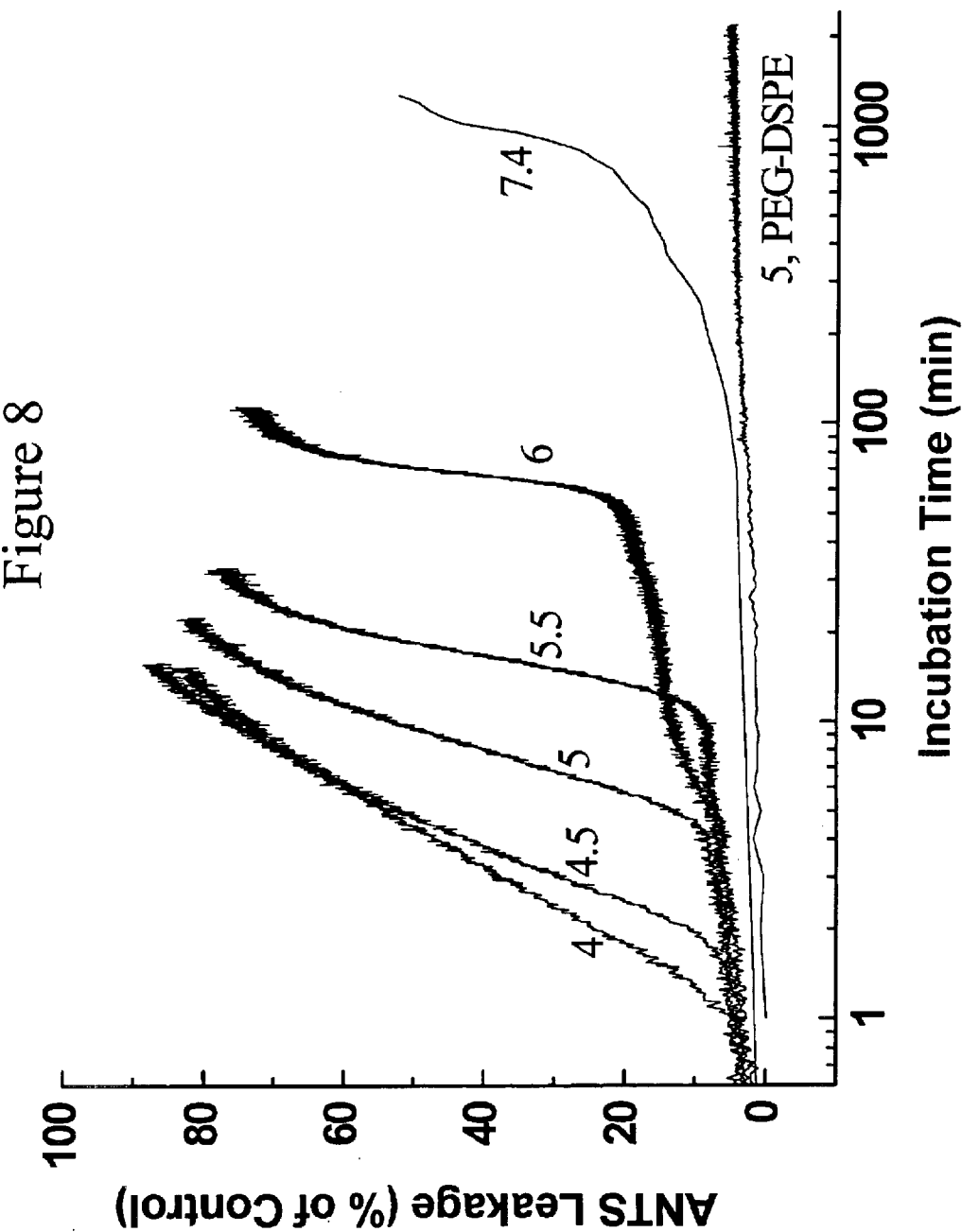
FIG. 8 shows the acid triggered content release from POD/DOPE liposomes as measured by ANTS leakage in buffers of different pH.

The POD compositions of the invention are suitable for use in liposomal drug delivery. POD/DOPE liposomes containing ANTS/DPX were used as a model system to determine that hydrolysis of POD can trigger the release of the contents from DOPE liposomes in response to a low-pH environment. The ANTS/DPX method is often used to study pH sensitive liposomal leakage since the fluorescence of ANTS is virtually unchanged from pH 4 to 8. When both compounds remain encapsulated, the fluorescence of ANTS is quenched by DPX. Upon leakage from the liposomes, ANTS is no longer quenched by DPX and gives an increase of fluorescent signal at 550 nm (excitation wavelength=370 nm). DSPE-PEG/DOPE (1/9) liposomes were incubated at pH 5 as a control. As shown in FIG. 8, the release of ANTS at different pH also occurs in two distinct phases, a lag phase, where a small portion of ANTS slowly leaks out of the liposomes, followed by a burst phase, when most of the ANTS is quickly released. The burst phase correlates well with the aggregation of the POD/DOPE liposomes in FIG. 7 and the collapse of the lamellar phase. As the liposomes are subjected to more acidic environments, the lag phase shortens. At pH 7.4, the lag phase lasts approximately 12 hours; at pH 6, the lag phase is reduced to 60 min; at pH 5, the lag phase is less than 5 minutes. As a control, ANTS/DPX was encapsulated into liposomes composed of 90% DOPE and 10% of a pH insensitive PEG lipid, DSPE-PEG. Less than 5% of the encapsulated ANTS was released over 12 hours when the vesicles were treated in the same way as the POD/DOPE liposomes even at the lowest pH. This confirms the role of acid catalyzed hydrolysis of the methoxyPEG-diortho ester-DSG conjugate in the leakage of the POD/DOPE liposomes.

Figure 9:
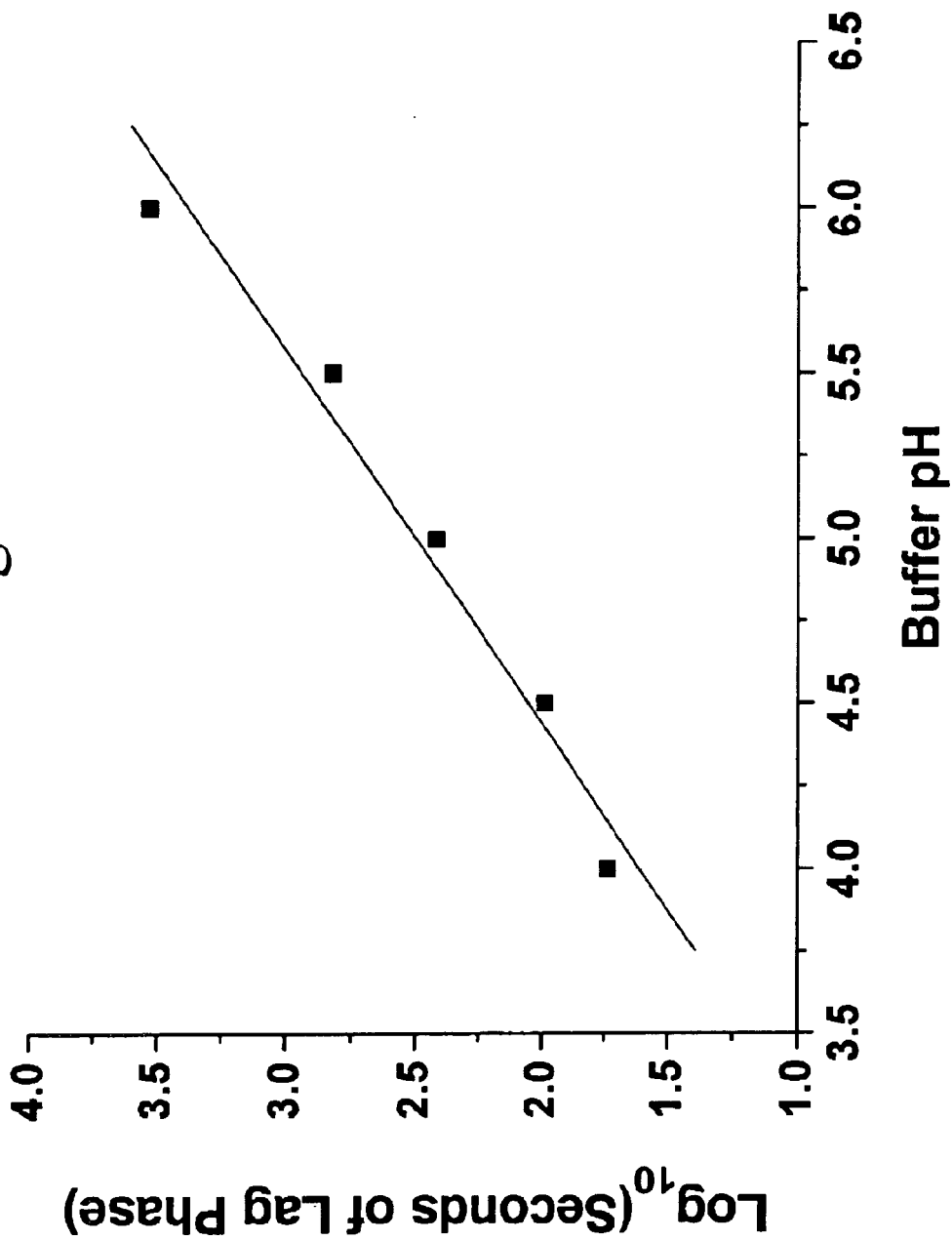
FIG. 9 gives the length of lag phase in buffers of different pH.

FIG. 9 shows a plot of the logarithm of the length of lag phase in FIG. 8 against buffer pH from 4 to 6 with a clear linear relationship. The logarithm of the length of lag phase in seconds is regressed versus the buffer pH to give: $\text{Log}_{10}$(Seconds of Lag Phase)=$-1.92+0.883 \times \text{pH}$, r=0.984. The lag time at pH 7.4 was not plotted in the graph since the transition is too slow to allow a precise determination. The slope of the regressed line is 0.883. This linear relationship demonstrates that the buffer pH plays a pivotal role on the kinetics of liposomal leakage.

Stability of POD Containing Liposomes in Serum

In serum stability assays, aliquots of fetal bovine serum (180 µL in each tube) in 0.6 mL tubes were pre-warmed at 37° C. for 30 min. An aliquot of stock liposome solution was diluted to 2 mM of total lipid by phosphate buffered saline (50 mM $NaH_2PO_4/Na_2HPO_4$ and 100 mM NaCl, pH 7.4), which had been pre-warmed at 37° C. for 30 min. An aliquot of the diluted liposome solution (60 µL) was then mixed with 180 µL pre-warmed fetal bovine serum to give a 75% final serum concentration. At different time points, a 20 µL aliquot was added into a polystyrene fluorimeter cuvette, containing 2 mL of HEPES buffered saline (5 mM HEPES and 145 mM NaCl, pH 8.5) at room temperature. The cuvette was covered with parafilm and inverted gently for 3–4 times. The fluorescence thus measured subtracted by the fluorescence of the buffer before the addition of the sample was taken as Ft. The Ft of an aliquot extracted and measured immediately after mixing a liposome sample with fetal bovine serum was taken as $F_0$. At the end of each assay an aliquot of the liposome-serum mixture was pipetted into 2 mL of HEPES buffered saline (5 mM HEPES and 145 mM NaCl buffer, pH 8.5), followed by adding the detergent dodecyloctaethylene glycol monoether ($C_{12}E_8$). The fluorescence measured after adding the detergent minus the fluorescence of the buffer was taken as $F_{100}$. Each data point of the leakage assay in fetal bovine serum represents the average and standard deviation of three independent samples.

Figure 10:
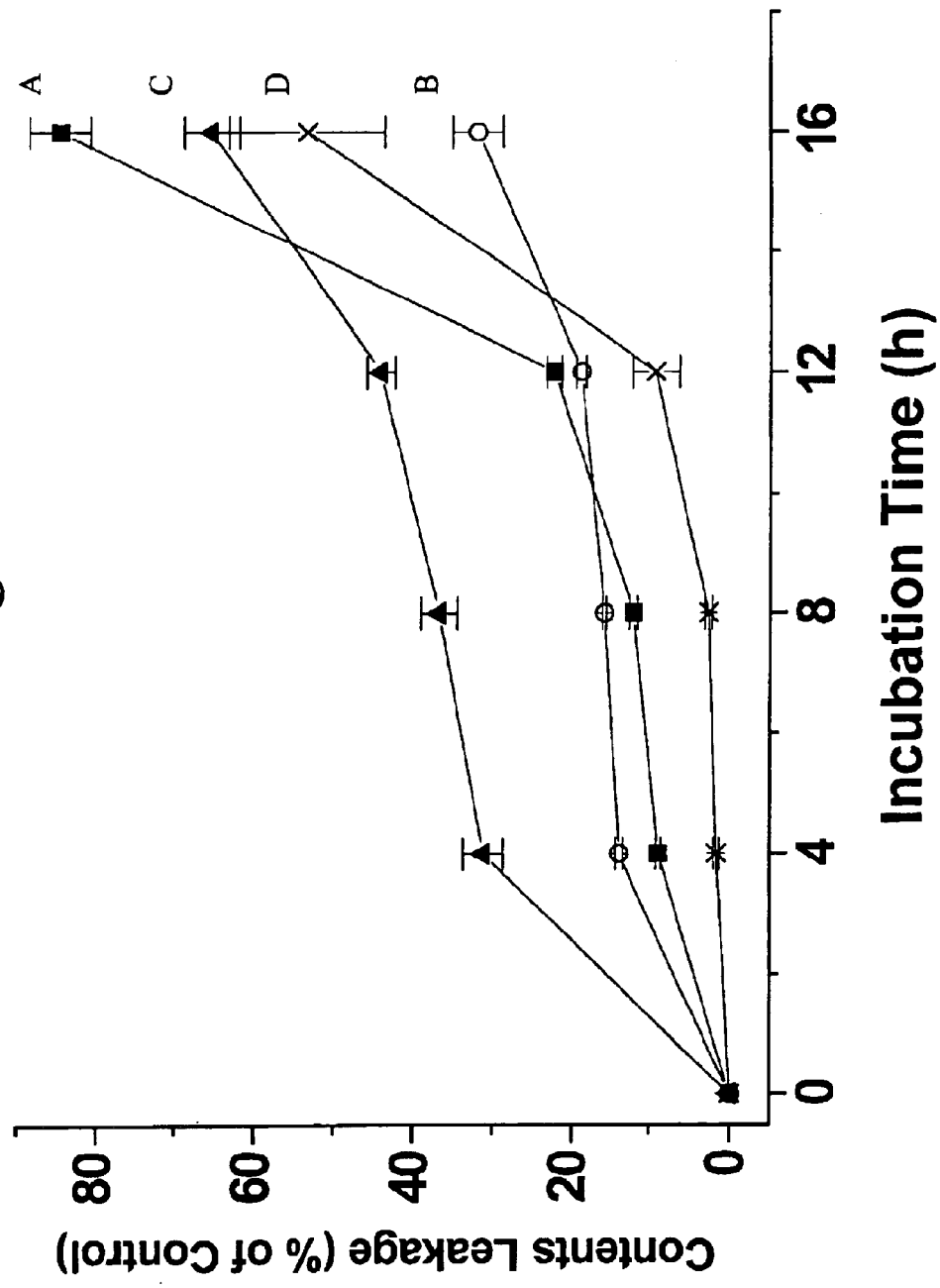
FIG. 10 represents the contents leakage from liposomes of various inventive and prior art compositions in 75% fetal bovine serum.

The addition of the LOCs helps stabilize liposomes in circulation. The in vitro stability of POD/DOPE (1/9) liposomes containing ANTS/DPX was tested by incubating with 75% fetal bovine serum at 37° C. and measuring the release of ANTS every 4 hours for 16 hours as shown in FIG. 10. For comparison, ANTS/DPX was also encapsulated into liposomes composed of DSPE-PEG/DOPE (1/9), CHEMS/DOPE (3/7), POPG/POPC/Chol (1/9/8) and the ANTS leakage was monitored in the same manner. (A) POD/DOPE (1/9); (B) DSPE-PEG/DOPE (1/9); (C)CHEMS/DOPE (3/7); (D) POPG/POPC/Chol (1/9/8).

POD/DOPE liposomes are relatively stable over 12 hours since less than 25% of the ANTS leaked out. However, after 16 hours of incubation, 84% of the ANTS was released, indicating a transition from the lag phase to the burst phase. The POD/DOPE liposomes were as stable as the pH-insensitive, PEG-stabilized DSPE-PEG/DOPE liposomes for the first 12 hours, but released ANTS much faster for the next 4 hours, indicating a liposome destabilization process specifically mediated by POD hydrolysis. In the first 12 hours of incubation, the POD/DOPE liposomes released 2 to 3 fold less ANTS than CHEMS/DOPE liposomes, whose excess negative charges from CHEMS tend to induce more interactions with serum components. The stable liposome formulation composed of POPG/POPC/Chol released less than 10% of the contents after 12 hours of incubation with serum. Thus, POD is able to stabilize liposomes in fetal bovine serum as effectively as traditional PEG-derived lipids for up to 12 hours, which is consistent with the ANTS leakage of these liposomes in HEPES buffered saline shown in FIGS. 8 and 9.

When incubated in 75% fetal bovine serum, POD stabilizes POD/DOPE (1/9) liposomes for up to 12 hours, a finding consistent with the long time for ANTS leakage of POD/DOPE liposomes in HEPES buffered saline at the same pH. Thus the stability characteristics vis-a-vis drug retention of liposomes comprising the LOCs of this invention are compatible for targeted delivery of encapsulated molecules given the observed intravenous elimination rate ($T_{1/2}$=194 min) of the formulation, which will be shown in the next section.

Stability of Liposomes in Blood Circulation

Blood clearance, distribution and excretion studies were conducted on 4-week-old female ICR mice (about 25 grams in weight) purchased from Simonsen (Gilroy, CA). All animals were handled in accordance with protocols established by the National Institute for Health Guidelines for the Care and Use of Laboratory Animals and with the approval of the Committee for Animal Research at the University of California, San Francisco. Animals were sacrificed at stated times with a sodium pentobarbital overdose.

p-Hydroxybenzamidine phosphatidylethanolamine (BPE) was synthesized and radiolabeled with Na $^{125}$I as previously described and the purity assessed by thin-layer chromatography. The labeled lipid contained less than 0.5% of free $^{125}$I. The labeled lipid, in chloroform solution, was added to POD/DOPE (1/9) or DSPE-PEG/DOPE (1/9) mixture in chloroform to yield 8.3×10$^{11}$ dpm/mol total lipid. Chloroform was evaporated under reduced pressure and the resultant lipid film was placed under high vacuum for 2 hours to remove the remaining solvent. The dried lipid film was hydrated with HEPES buffered saline (10 mM HEPES and 145 mM NaCl, pH 7.4) over 20 min by intermittent agitation on a vortex mixer and the suspension extruded three times through a 0.1 μm polycarbonate membrane. The diameter of the extruded liposomes, as measured by Photon Correlation Spectrometry, was 140–160 nm. Each mouse received a tail-vein injection of 150 μL of the extruded liposomes containing 0.9 μmol total lipid.

At various time points following administration of $^{125}$I labeled liposomes, animals were anesthetized with inhalation of isofluorane. Approximately 50 μL of blood was collected with a glass pasteur pipette from the orbital sinus vein, weighed and its γ-activity measured in Beckman Gamma 8000 (Fullerton, Calif.). The γ-activity in whole blood and hence, the percentage of dose remaining in the blood was calculated assuming 0.07 g of blood per gram of animal weight. The average and standard deviation of samples collected from three animals were presented.

Figure 11:
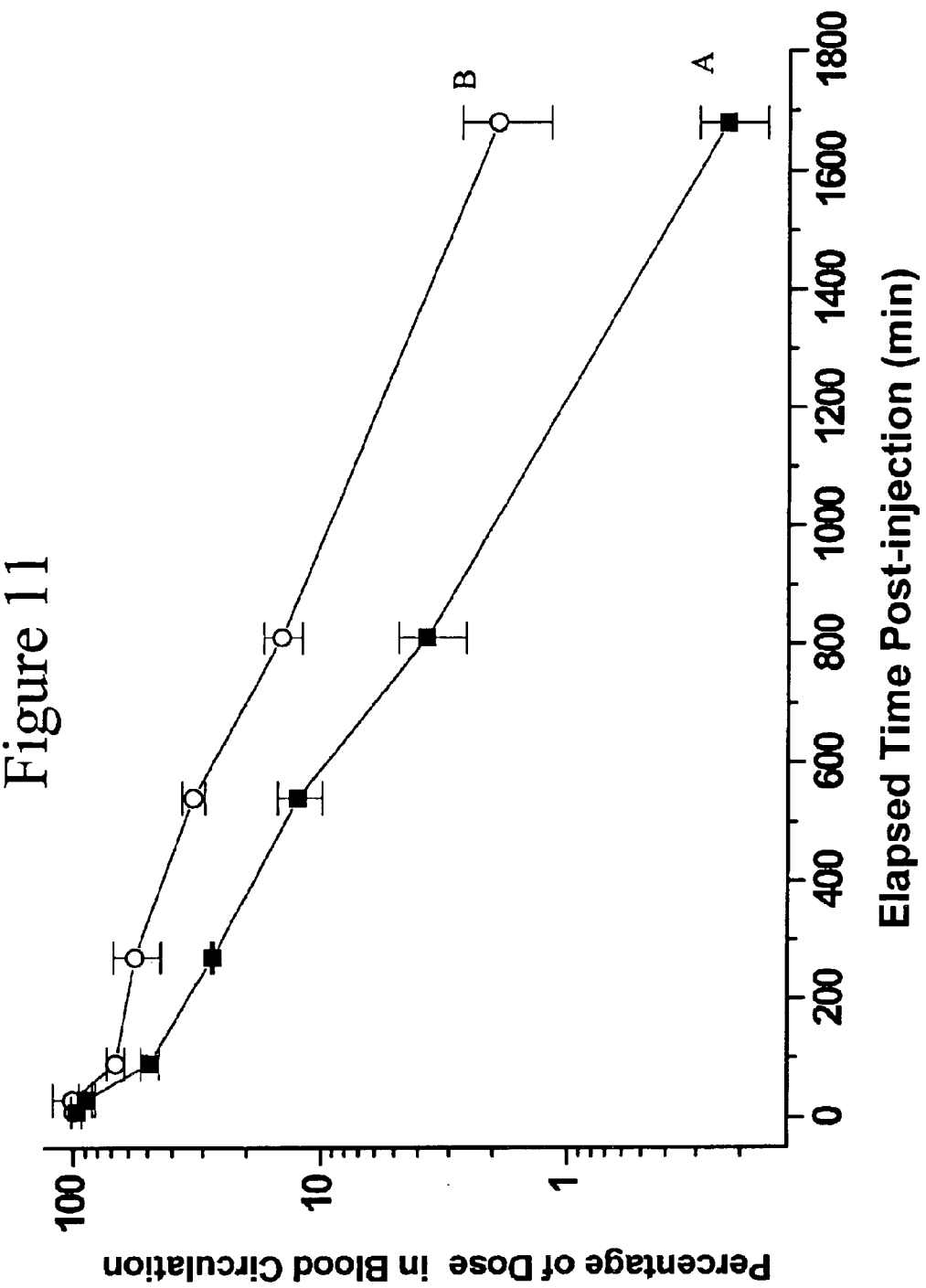
FIGS. 11–12 show the clearance of radioactive-labeled inventive and prior art liposomes from circulation.
Figure 12:
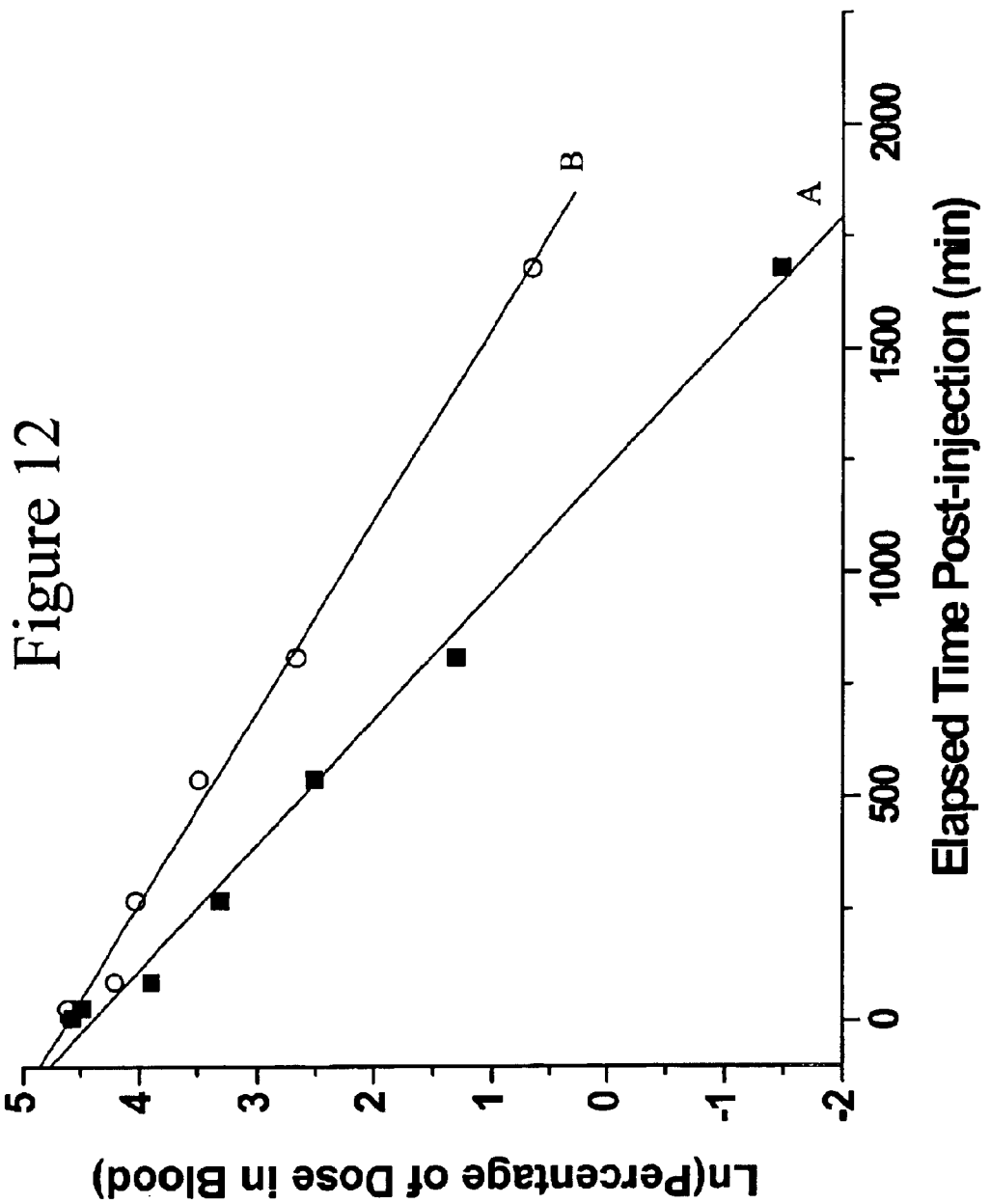

The LOCs of the invention have a steric-stabilizing effect on liposomes in vivo. FIGS. 11 and 12 show the rate of elimination from blood of radiolabeled liposomes composed of 10% POD and 90% of DOPE that were injected into the tail-vein of female ICR mice. For comparison, we also administered radiolabeled liposomes composed of 10% DSPE-PEG, a pH-insensitive lipid-PEG conjugate, and 90% DOPE. Liposomes composed of pure DOPE are not stable enough at pH 7.4 to allow their injection into animals. The graphs show the clearance of 1-BPE POD/DOPE (1/9) liposomes (A) and $^{125}$I-BPE DSPE-PEG/DOPE (1/9) liposomes (B) from circulation. In FIG. 11, the percentage of injected dose remaining in blood (n=3, mean±S.D.) is plotted against the elapsed time post-injection. In FIG. 12, the natural logarithm of the percentage of dose remaining in blood is plotted against elapsed time post-injection and regressed to obtain the liposomal half-life. For PODIDOPE (1/9) liposomes, Ln(Percentage of Dose in Blood)=4.41-0.00358×(min), r=0.997, $T_{1/2}$=Ln2/0.00358=193.6 min. For DSPE-PEG/DOPE (1/9) liposomes, Ln(Percentage of Dose in Blood)=4.62-0.00235×(min), r=0.997, $T_{1/2}$=Ln2/0.00235=295.0 min. For both POD/DOPE and DSPE-PEG/DOPE liposome formulations, the percentage of injected dose remaining in circulation showed a single log-linear decay with a correlation coefficient constant greater than 0.995, indicating a one-compartment clearance kinetics. The blood clearance profile of the POD/DOPE liposomes is more similar to the pH insensitive sterically stabilized DSPE-PEG/DOPE liposomes than to conventional liposomes, which usually exhibit a two-compartment elimination kinetics. The half-life of the POD/DOPE liposome and the DSPE-PEGIDOPE liposome is about 194 and 295 minutes, respectively. This reasonably close correspondence of the elimination rate between the two formulations is strong evidence that the PEG head group in the pH sensitive ortho ester conjugate provides a steric-stabilizing effect on the fusogenic DOPE liposomes in circulation.

The half-life of liposomes comprising the LOCs of this invention circulation, as exemplified by the POD/DOPE formulation, is similar to other formulations that consist primarily of DOPE and that are stabilized by PEG. Such formulations predictably have a shorter serum half-life than the traditional sterically stabilized formulations that consist of saturated phosphatidylcholine/Chol/PEG-DSPE. Such a composition yields an inherently more rigid bilayer that is capable of resisting the penetration of serum components that might contribute to a more rapid elimination of a liposome even when it has a steric coat. Thus, further improvements of the serum half-life and drug release characteristics in alternative embodiments can be achieved by modification of the liposomes of the invention by the inclusion of cholesterol in the formulation, or by other comparable modifications.

Distribution and Excretion of Liposomes

At various time points following administration of $^{125}$I labeled liposomes, animals were anesthetized with an intraperitoneal (i.p.) injection of 100 μL anesthetics cocktail (44 mg/kg ketamine, 2.5 mg/kg xylazine and 0.75 mg/kg acepromazine). Approximately 1 mL of blood was removed via intracardiac puncture. One milliliter of phosphate-buffered saline (containing 0.2 g/L $KH_2PO_4$, 2.16 g/L $Na_2HPO_4 \cdot 0.7H_2O$, 0.2 g/L KCl and 8.0 g/L NaCl) was perfused through the right cardiac ventricle. The heart, lungs, liver, spleen, kidneys, stomach, intestines, head, mid section and tail were collected, weighed and the radioactivity counted in the Beckman Gamma 8000. The γ-activity in whole blood and hence the percentage of dose remaining in the blood was calculated assuming 0.07 g of blood per gram of animal weight. The average and standard deviation of samples from three animals were reported.

Figure 13:
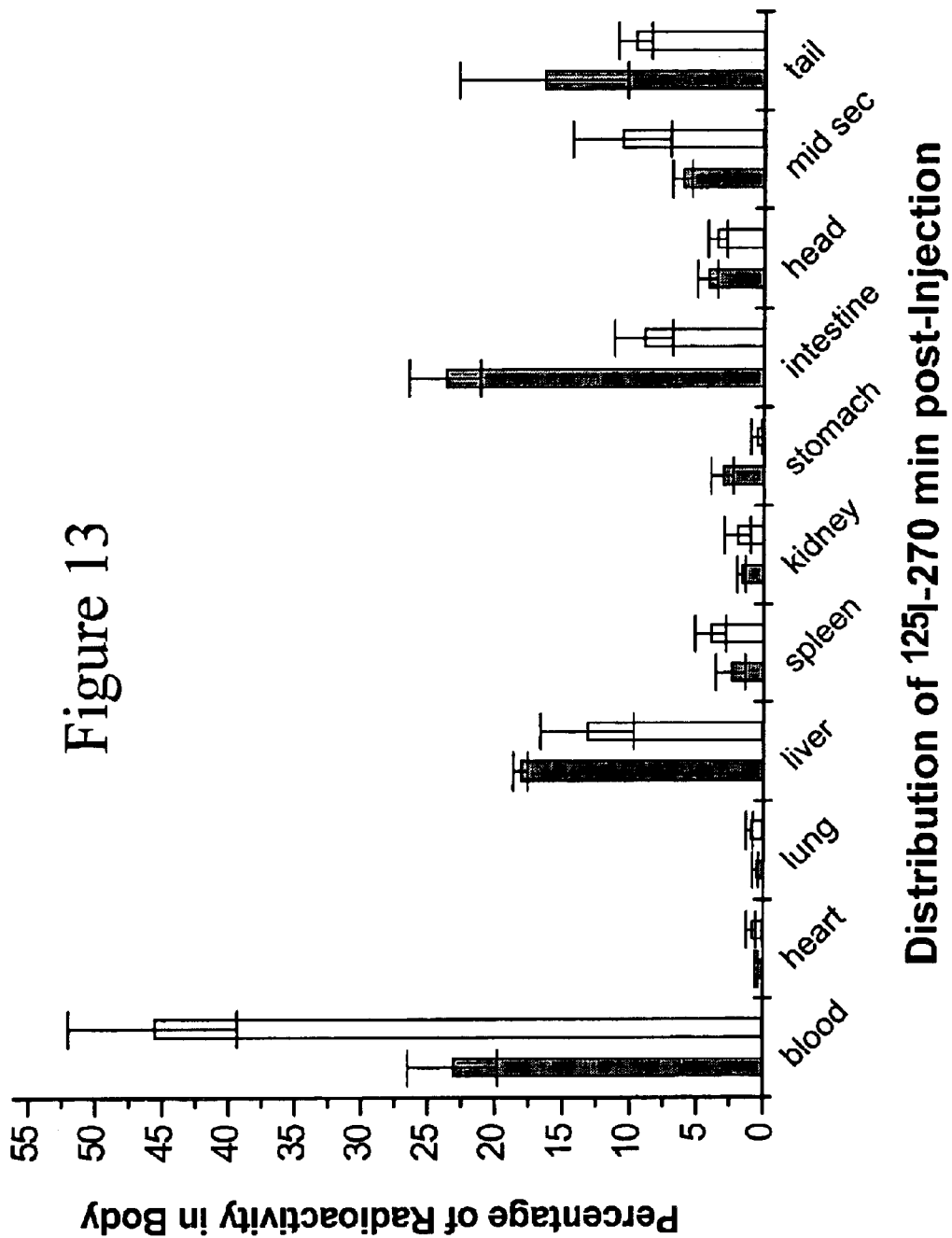
FIGS. 13–15 show the distribution of radioactive-labeled inventive and prior art liposomes at different times after injection.
Figure 14:
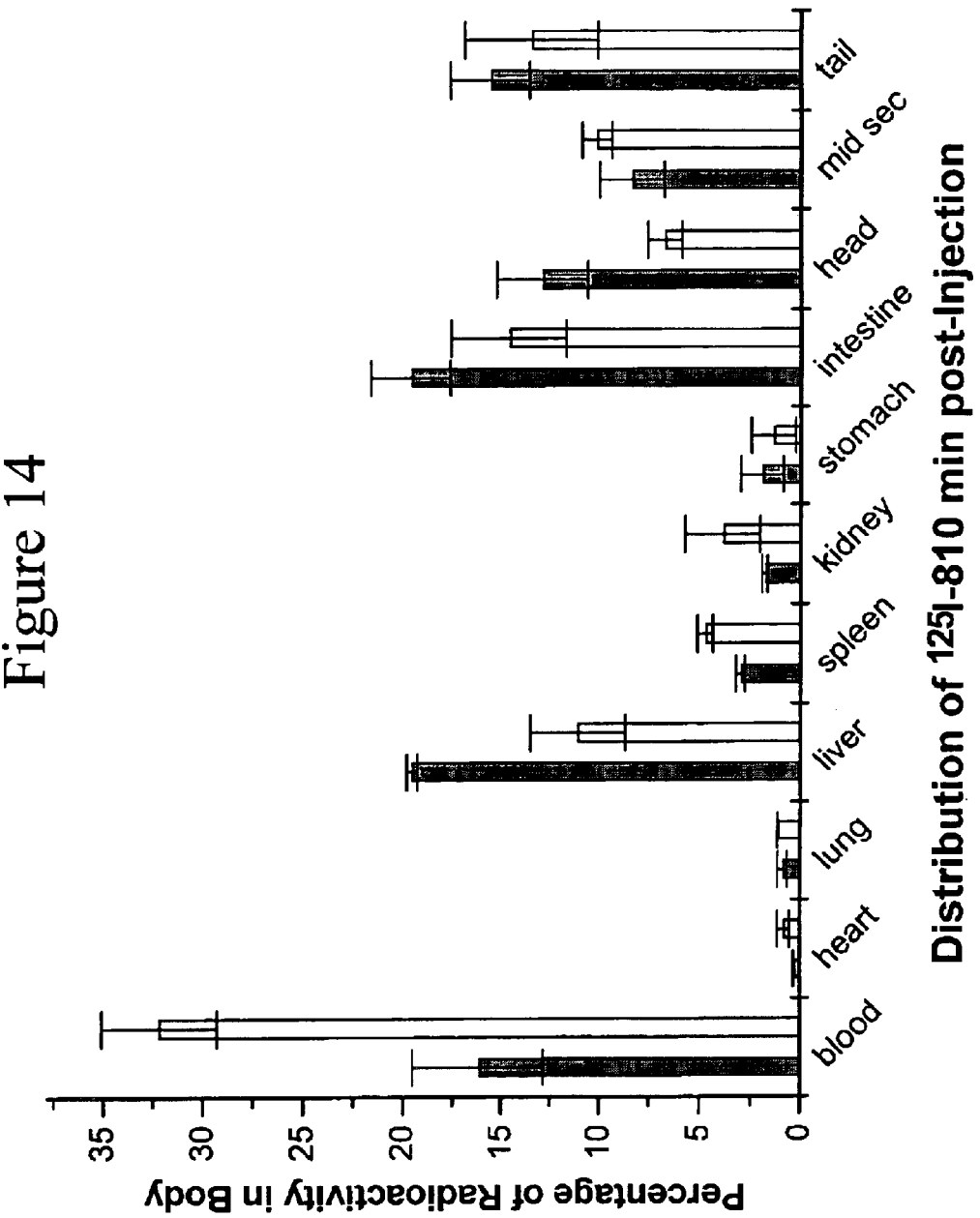
Figure 15:
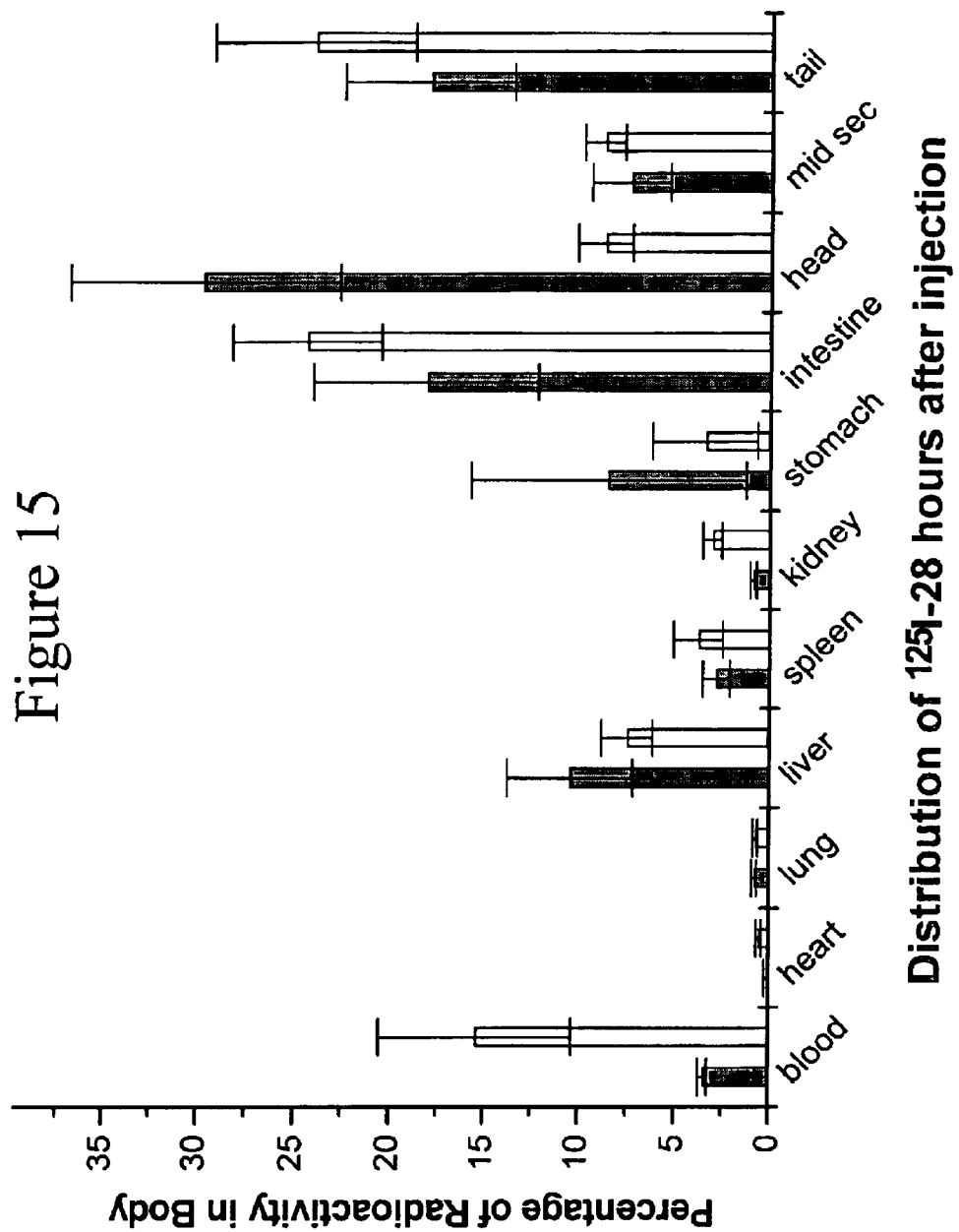
Figure 16:
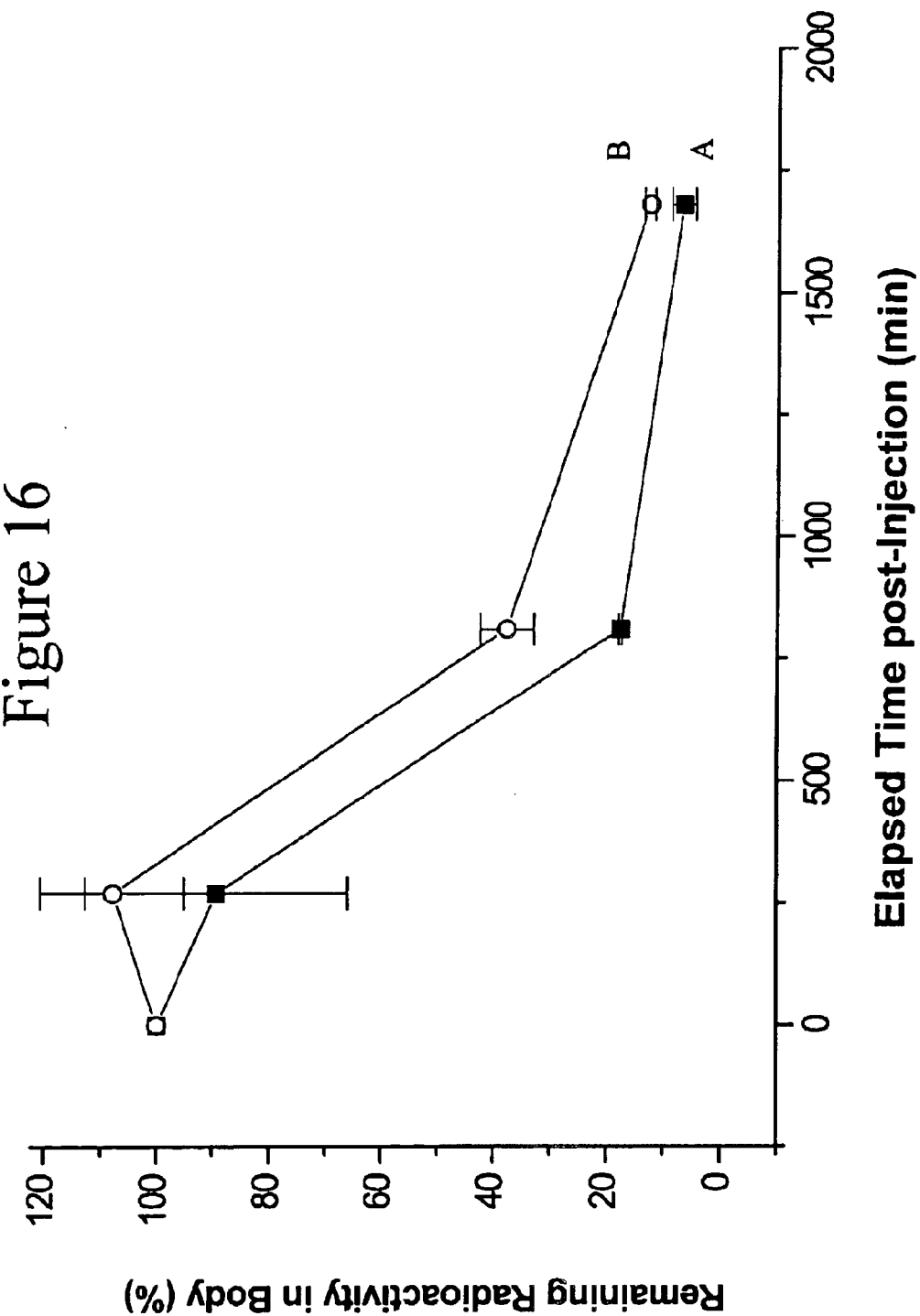
FIG. 16 shows the excretion kinetics of radioactive-labeled inventive and prior art liposomes.
Figure 18:
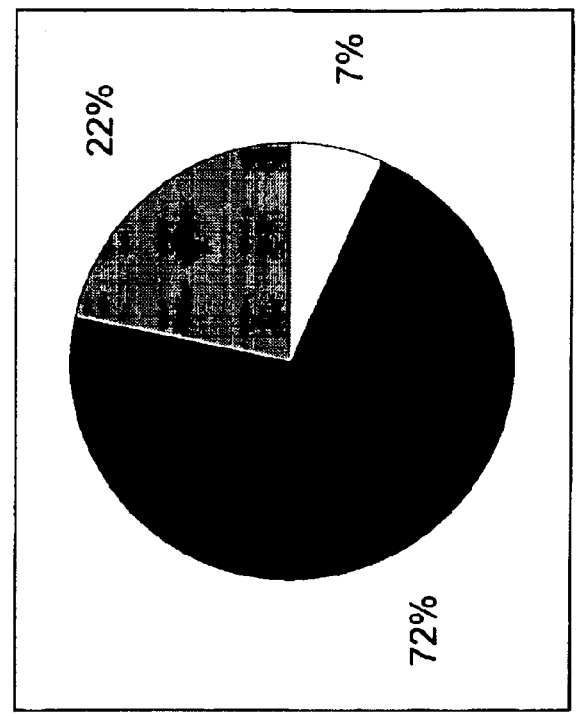
FIGS. 17–18 graphs the mass balance of injected radio-labeled liposomes.
Figure 17:
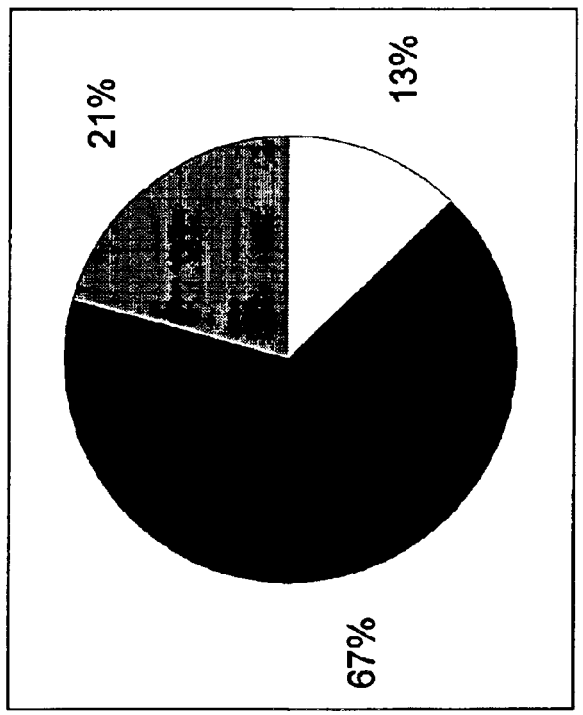

The distribution of radiolabeled POD/DOPE liposomes was measured by assessing measured the radioactivity associated with different organs of mice at 270 minutes, 810 minutes and 28 hours following liposome injection. It is known that $^{125}$I-labeled BPE is metabolized only after being endocytosed together with the liposomes. The urine and the feces were also collected at the 28-hour time point and their radioactivity measured to determine the routes of $^{125}$I excretion. The results are shown in FIGS. 13–15. As shown in FIG. 13, at 270 minutes post-injection about 20% of POD/DOPE liposomes and 45% of DSPE-PEG/DOPE liposomes remained in circulation. The graphs show the distribution of $^{125}$I radioactivity of POD/DOPE (1/9) (solid bars) and DSPE-PEG/DOPE (1/9) (open bars) liposomes in female ICR mice at 270 min, 810 min and 28 h post-injection, respectively. (n=3, mean±S.D.) For both formulations, the liver and intestine were the two major organs of radioactivity disposition. The excretion of $^{125}$I radioactive POD/DOPE (1/9) (A) and DSPE-PEG/DOPE (1/9) (B) liposomes was also determined. At later time points (810 minutes and 28 hours post-injection), most of the radioactivity of both formulations was excreted from the animals as shown in FIG. 16, while the liver and intestine were the major organs for the disposition of the remaining radioactivity in the body as shown in FIGS. 14 and 15. Twenty-eight hours after injection, the residual radioactivity from POD/DOPE liposomes was distributed preferentially to the head (shown in FIG. 15), probably due to an accumulation of the iodine in the thyroid followed by a slow clearance of $^{125}$I from this organ. In FIGS. 17–18 the $^{125}$I radioactivity of POD/DOPE (1/9) (FIG. 17) and DSPE-PEG/DOPE (1/9) (FIG. 18) liposomes from all parts of body (white), urine (black) and feces (gray) were measured 28 hours post-injection and plotted in percentage of the total radioactivity recovered. The percentage of injected dose recovered is 110% for POD/DOPE liposomes and 93% for DSPE-PEG liposomes. This shows for both formulations at 28 hours post-injection, about 70% of radioactivity was excreted into urine and about 20% was found in feces. Overall, POD/DOPE liposomes were eliminated from circulation about 50% faster than DSPE-PEG/DOPE liposomes but the patterns of distribution and excretion of the two formulations were very similar. Based on the distribution and the excretion data, the formulations were cleared mainly by liver from circulation, after which the $^{125}$I BPE labels were degraded and excreted into urine and bile.

Alternative embodiments of the invention can be tailored to situations where the target to which a drug or gene is directed are located in a target organ that receives only a small fraction of the total blood flow. Drug carriers that are eliminated from circulation too rapidly cause the amount of drug carrier that enters the target organ to be too low to provide an optimal therapeutic effect. This invention allows the creation of liposomes or lipid bodies comprising of PEG or other protective coverings, which are provided by the cleavable head groups of the LOCs. The liposomes or lipid bodies circulate for a long time but once in the target site, the local low pH causes the protective covering to come off and allows the liposomes to be taken up by the target cells. Examples of the pharmacokinetics and tissue distribution of the compositions of the invention are shown in FIGS. 11–18.

EXAMPLE 2

In another embodiment of the invention, the LOCs can be incorporated into a long circulating fusogenic phosphatidylethanolamine (PE) liposome containing encapsulated plasmid DNA. The plasmid DNA can be encapsulated either as a naked polymer or as a complex with other suitable cations such as cationic polymers or cationic lipids. The ability of liposomes containing DNA to deliver the DNA requires that the liposome enters the target cell. Liposomes comprising PE have a propensity to fuse with other membranes due to their lipid composition. However such liposomes are inherently unstable unless mixed with other lipids. Lipids with PEG-headgroups are particularly good for stabilizing PE liposomes, but conventionally deprive the liposome of its fusogenic activity. Conversely, PE liposomes comprising the LOCs of the invention such as POD are stable until the PEG coat is removed. Once the methoxyPEG hydrolyzes from the POD, the liposomes can fuse with the target membranes.

Liposomes containing a DNA plasmid encoding for the human alpha-1-antitrypsin gene were prepared by the reverse phase evaporation method U.S. Pat. No. 4,394,448, incorporated herein by reference in its entirety, from a lipid composition 10 mole percent methoxypolyethylene glycol 2000-diortho ester-distearoyl glycerol conjugate and 90 mole percent dioleoylphosphatidylethanolamine in a pH 9.0, 30 mM Tris-HCl-5% glucose buffer. Thirty μmoles total lipid was suspended in 3 mL diethylether and 1.0 mL Tris-glucose buffer containing 600 μg plasmid DNA. The liposome encapsulated plasmid DNA was separated from non-encapsulated DNA on a Ficoll gradient. Following separation, the liposomes were stored at 4° C. until injection into an animal. In a similar fashion plasmids containing other genes, such as those coding for factor VIII or other classes of nucleic acids such as oligonucleotides or RNA can be encapsulated into liposomes composed of PE containing the pH sensitive ortho ester PEG lipid. As shown in FIGS. 11 and 12, liposomes with such a composition have a prolonged circulation time after injection but will rapidly collapse and fuse with the endosomal membrane after being taken up into a low-pH compartment via endocytosis. After fusing with the endosomal membrane the encapsulated nucleic acid is transferred into the cytoplasm.

EXAMPLE 3

Figure 19:
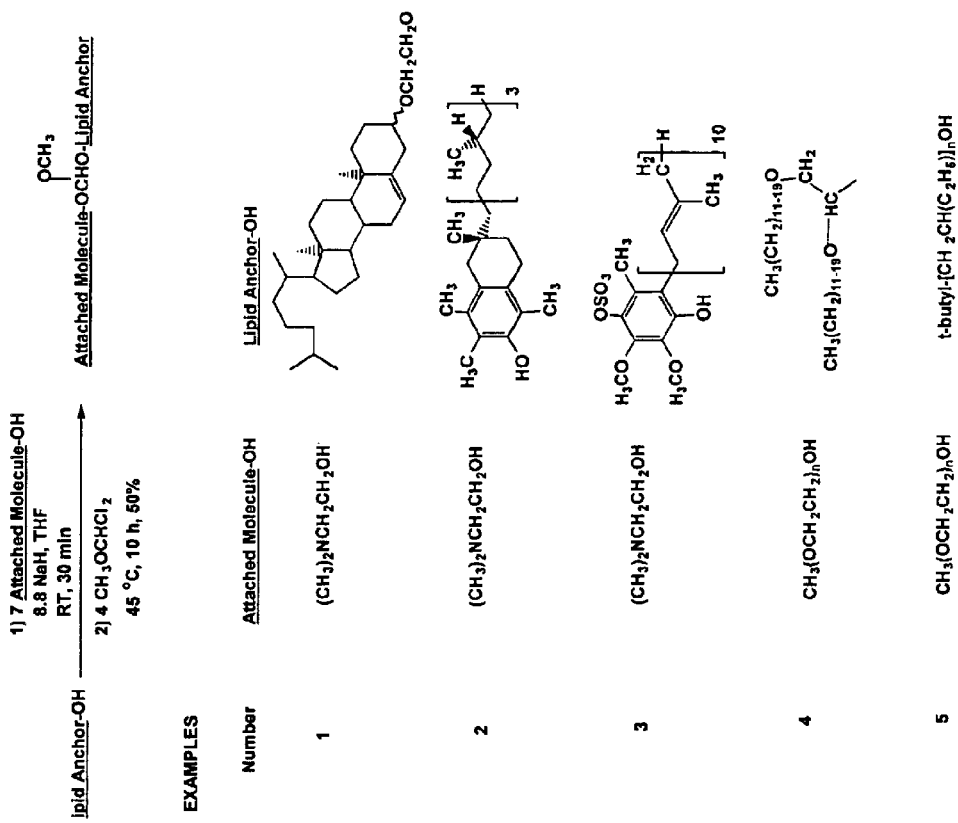
FIG. 19 shows the general synthesis for compositions of the invention comprising dichloromethylmethyl ether.

The LOCs of the invention may also comprise cationic lipid derivatives comprising a cationic hydrophilic portion, a hydrophobic portion and an ortho ester linker. In this embodiment a single ortho ester derived from dichloromethylmethyl ether is used. Such ortho ester conjugates may be synthesized using dichloromethylmethyl ether as shown in FIG. 19. Detailed procedures for preferred embodiments are described below.

N,N-dimethyl-(4-methoxy-(cholest-5-en-3β-oxy)hept-3,5-dioxa-yl) amine (DOC)

In this embodiment, a THF (anhydrous, 50 mL) solution of cholest-5-en-3β-oxyethan-2-ol (400 mg, 0.926 mmol)

and N,N-dimethylethanolamine (630 mg, 0.71 mL, 7 mmol) under Ar was prepared and sodium hydride (352 mg, 60% dispersion in mineral oil, 8.8 mmol) added. The reaction mixture was stirred at room temperature for 30 minutes. Dichloromethyl-methyl-ether (4 equiv) was then injected in one bolus while the reaction mixture was vigorously stirred. The reaction mixture was then stirred at 45° C. under Ar for 10 h. Triethylamine (1 mL) was added and the reaction mixture was filtered. The precipitate was extracted with 1% of triethylamine in $CHCl_3$ and the extract was pooled with the filtrate and evaporated under reduced pressure. The residue of the evaporation was dissolved with minimum volume of $CHCl_3$/MeOH/triethylamine (100/5/0.5, vol/vol/vol). A silica gel column (40 g) was equilibrated with $CHCl_3$/MeOH (100/5) and then treated with 20 mL of $CHCl_3$/MeOH/triethylamine (100/5/0.5, vol/vol/vol). The solution of the evaporation residue was then loaded on top of the column and eluted with $CHCl_3$/MeOH/triethylamine (100/5/0.5, vol/vol/vol) to yield 264 mg (51% purified yield) of the product.

N,N,N-trimethyl-(4-methoxy-(cholest-5-en-3β-oxy)hept-3,5-dioxa-yl)amine Iodide

Figure 20:
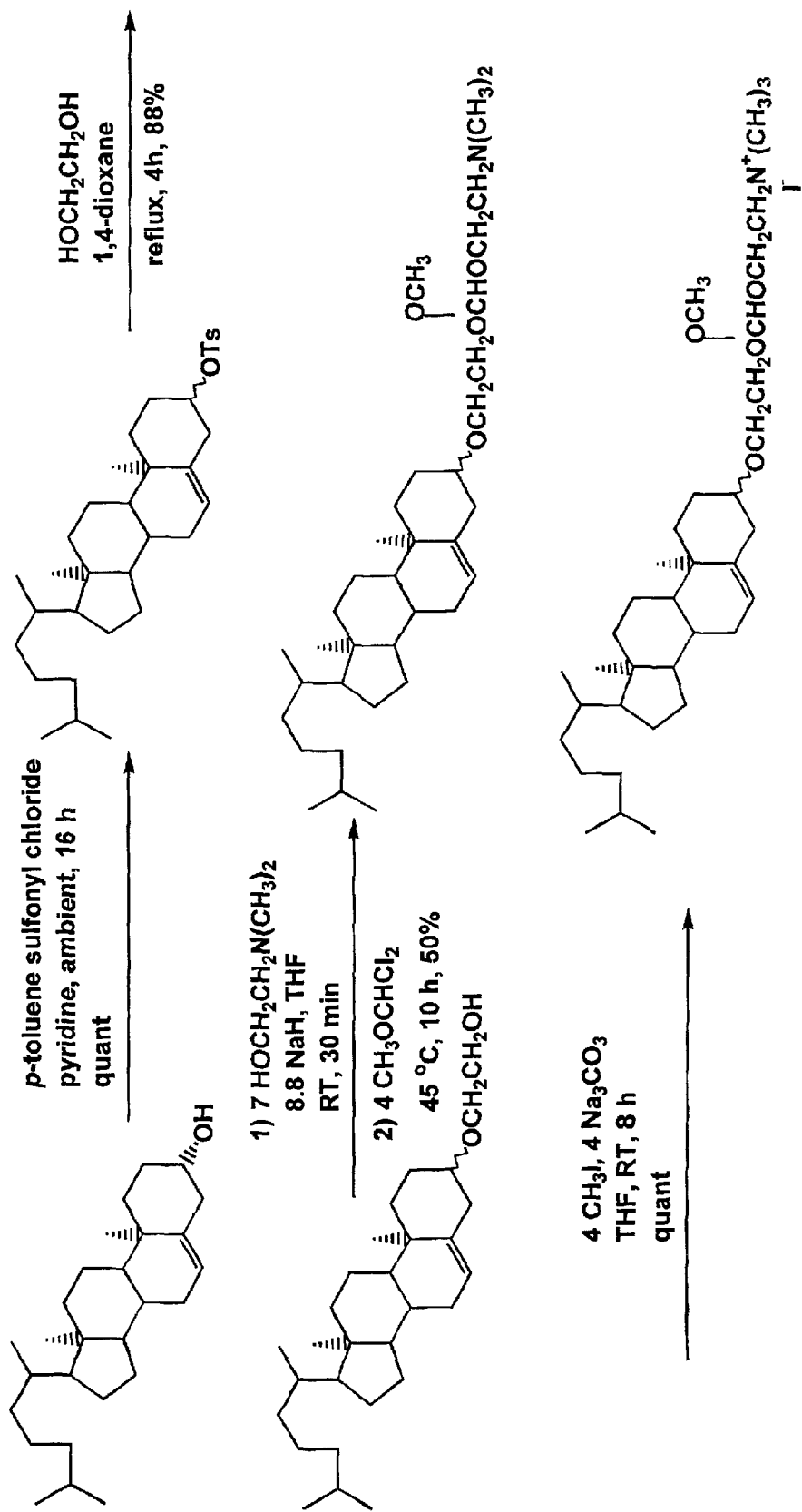
FIG. 20 shows the synthesis of an alternative embodiment of an LOC of the invention, using dichloromethylmethyl-ether as the linker molecule.
Figure 21:
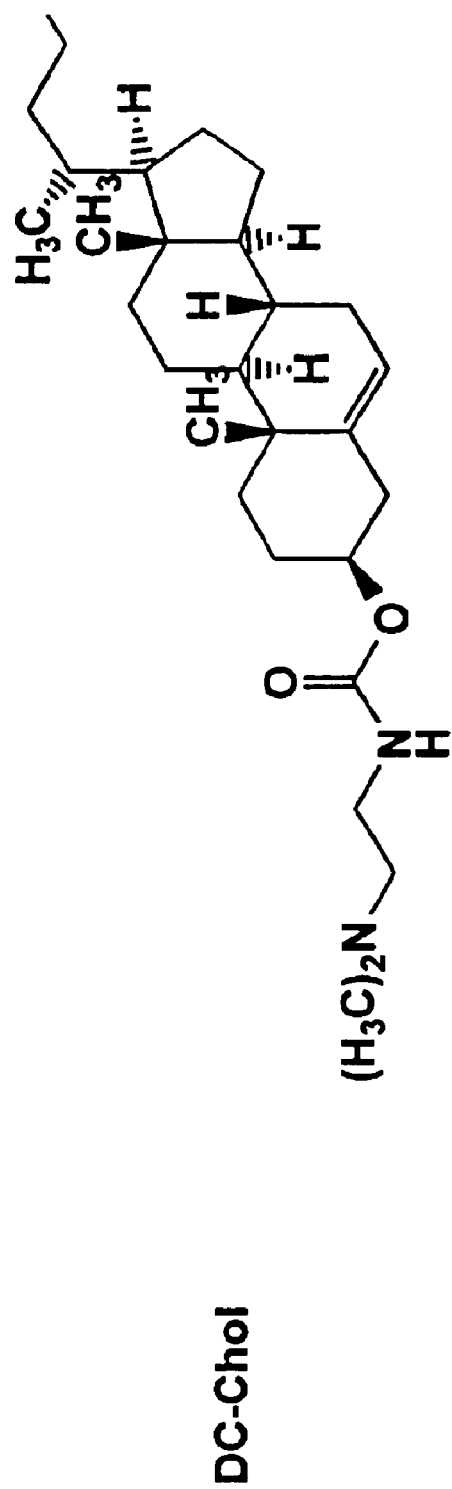
FIG. 21 shows of the structure of DCChol.

As an alternative embodiment of the previous reaction, ortho ester based pH-sensitive quanternary amines could be prepared by methylation of the corresponding tertiary amine as shown in FIG. 20. Thus N,N-dimethyl-(4-methoxy-(cholest-5-en-3β-oxy)hept-3,5dioxa-yl)amine (180 mg, 0.32 mmol), methyl iodide (100 μL, 1.6 mmol, d=2.28) and sodium carbonate (200 mg, 1.9 mmol) were suspended in THF (5 mL) under Ar at room temperature for 8 hours. TLC showed the disappearance of the spot of N,N-dimethyl-(4-methoxy-(cholest-5-en-3β-oxy)hept-3,5-dioxa-yl)amine and the generation of a new more hydrophobic spot, presumably the methylation product. The TLC of the reaction was very clean, strongly suggesting a quantitative reaction. The Electrospray Mass Spectrometry shows the peak at m/z 576.5, corresponding to the cationic ortho ester conjugate without the negative counter ion.

Additional Embodiments

Additional reactions can be carried out using similar conditions. Polyethyleneglycol as well as another hydrophobic alcohol can be readily dissolved in THF. A chromatography system with appropriate ratio of $CHCl_3$/MeOH/triethylamine can be used as the eluting solvent to separate the products. The ortho ester conjugates should be more polar than the hydrophobic alcohols (lipid anchors) but less polar than the hydrophilic alcohols (attached molecules, or head groups), and hence be resolvable by the recommended chromatography system.

In Vitro Transfection Using Doc Liposomes

Luciferase plasmid was transfected into CV-1 cells using the pH-sensitive cationic lipid, DOC. In comparison, a pH-insensitive cationic lipid, DCChol, which possesses a similar chemical structure as that of DOC, was also used for gene transfection. The charge ratio of the complexes was varied from 5/1 to 1/1. The positive charges correspond to the amine group of DOC and the negative charges correspond to the DNA phosphate. 0.3 to 3 μg of plasmid DNA was used per well in a 24 well-plate. The ratios of the lipid components (DOC, DOPE, DCChol) are in mole. 3 μg of luciferase plasmid DNA alone, DNA-3, was added to the CV-1 cells as a control of transfection without using any cationic liposomes. Transfection efficiency was determined by measuring the relative light units (RLU) to indicate the enzyme activity of the gene product of the luciferase plasmid DNA. As can be seen in Table 1, at appropriate charge ratios and plasmid DNA doses, DOC/DOPE liposomes are significantly more efficient than the DCChol/DOPE liposomes in transfecting the CV-1 cells. No transfection was observed for the DNA-3 control. Specifically, at charge ratio 5/1 and plasmid DNA dose of 3 μg per well, DOC/DOPE is about 10 fold more effective then the DCChol/DOPE (~5.6× $10^8$ RLU/mg cellular protein vs. ~0.56×$10^8$ RLU/mg cellular protein) and at charge ratio 3/1 and plasmid DNA dose of 3 μg per well, DOC/DOPE is about 7 fold more effective then the DCChol/DOPE (~8.4×$10^8$ RLU/mg cellular protein vs. ~1.2×$10^8$ RLU/mg cellular protein).

TABLE 1

Transfection of Cationic Lipoplexes in CV-1 Cells (RLU/cellular protein)

| | DOC/DOPE (1/1) | | DCChol/DOPE (1/1) | |
| --- | --- | --- | --- | --- |
| (+/−)-dose | Mean | Std Dev | Mean | Std Dev |
| 5/1-3 μg/well | 5.68 × $10^8$ | 1.64 × $10^8$ | 5.75 × $10^7$ | 2.58 × $10^7$ |
| 3/1-3 μg/well | 8.34 × $10^8$ | 4.04 × $10^8$ | 1.26 × $10^8$ | 7.90 × $10^8$ |

In Vivo Transfection Using Doc Liposomes

The increased effectiveness for gene transfer observed in cell culture for the pH sensitive ortho ester derivative compared to the non-ortho ester control cationic lipid is also observed after intratracheal administration of the complexes into mice as shown in Table 2. Lipoplexes were prepared having a 5/1 charge ratio and 5 μg plasmid DNA in 100 μL buffer were administered per animal. The lipid compositions are in molar ratio. The DOC/DOPE-DNA lipoplexes are about 5- to 6-fold as efficient as DC-Chol/DOPE-DNA lipoplexes in transfecting murine lungs following intratracheal administration.

TABLE 2

Intratraceal Transfection in Female ICR Mice (RLU/mg protein)

| | DOC/DOPE (1/1) | | DCChol/DOPE (1/1) | |
| --- | --- | --- | --- | --- |
| | Mean | Std Dev | Mean | Std Dev |
| Heart | 567.4 | 450.7 | 0 | 0 |
| Lung | 267872.7 | 149984.4 | 48136.2 | 17863.9 |
| Liver | 326.5 | 236.1 | 62.2 | 71.3 |
| Spleen | 5462.9 | 9342.2 | 0 | 0 |

EXAMPLE 4

Some compounds of the invention may be used to mask targeting ligands to prevent their premature interaction with cellular receptors. There are a number of situations where the receptor to which a drug- or gene-carrier binds is located both on the target tissue and also on a non-target tissue. What differentiates the two possible tissues, is that the non-target tissue is located at the point of administration of the drug carrier into the body whereas the target tissue is found at a site remote from the point of administration of the drug carrier. This often happens in the case of targeting of a drug carrier to a tumor. The drug carrier is administered into the blood stream where it first interacts with the various cells in immediate contact with the blood before it can reach the tumor. If the drug carrier is entrapped by the non-target tissue before it can interact with the target tissue, toxicity can result and the therapy will not be effective. Target ligands that are suitable for use with the invention comprise hyaluronan, antibodies, peptides, folate, receptor antagonists, carbohydrates, transferrin, protein hormones, and cytokines.

For instance, there are a number of receptors that can interact with hyaluronic acid. One receptor that interacts with hyaluronic acid, CD44, is located on various types of tumors including breast tumors, colon tumors, melanomas, prostate tumors and certain lung tumors. A second receptor that interacts with hyaluronic acid is located on endothelial cells in the liver. If an appropriate hyaluronan ligand is attached to a drug carrier, such as a liposome and the modified liposome is then injected into an animal, the modified liposome is removed from circulation as it passes through the liver by the hyaluronan endothelial receptor in the liver. The carrier therefore does not have the opportunity to interact with the CD44 receptor in the tumor. Accordingly, it is advantageous to mask the targeting ligand until the delivery system is in the vicinity of the tumor. This can be done by incorporating the LOCs of the invention into the liposome with the targeting ligand. For example, POD can be used to mask the hyaluronan ligand on the liposome surface and prevent it from interacting with the receptor in the liver. The liposome can then circulate and lodge in the tumor. Tumors have a slightly lower pH than do other sites in the body, hence POD is hydrolyzed and its head group, methoxyPEG removed from the liposome surface more rapidly in the tumor. As the methoxyPEG is released from the liposome, the hyaluronan as a targeting ligand is exposed and can now interact with the CD44 receptor on the tumor cell surface. This leads to preferential uptake of the targeted liposome by the tumor and not by the endothelial cells in the liver.

Lipid films can be prepared by drying 10 μmoles of lipid including a targeting ligand for the CD44 receptor, DPPE-hyaluronan (HA-DPPE), the polyethylene glycol 2000-diortho ester-distearoyl glycerol conjugate (POD), cholesterol (Chol) and Distearoylphosphatidycholine (DSPC) under vacuum using rotary evaporator at room temperature. Liposomes (comprising the lipids: DSPC:Chol:HA-DPPE:POD in the mole ratio of 51:40:3:6) are prepared by rehydrating the lipid film with 1 ml of 10 mM Tris/HCl, 120 mM ammonium sulfate (pH 9.0), followed by aggitation on a vortex mixer for 1 minute, and extrusion through 0.2 and 0.1 μm polycarbonate membranes. Liposomes are loaded with doxorubicin by a remote loading technique and stored at 4° C. under argon. Doxorubicin loaded liposomes are used within one day of preparation. Two different control liposomes are used: in the first the POD is $C_1$ not included in the lipid formulation. In the second control liposome, a non-pH sensitive PEG-DSPE replaces the POD in the liposome composition. The hydrodynamic diameter of the liposomes is determined by dynamic light scattering. (Malvern Instruments, UK). The liposomes so formed can be frozen, freeze dried, lyophilized or converted into dry powders using standard conditions to those skilled in the art to create stabilized pH sensitive formulations with prolonged shelf-life. Such methods are disclosed in U.S. Pat. No. 5,811,406 which is hereby incorporated in its entirety by reference.

The various formulations are tested in a CD44 positive breast cancer tumor, the MDA-MB-435 tumor line. The MDA-MB-435 tumor cells (0.2 mL of a $1 \times 10^7$ cells/mL suspension in PBS) are injected subcutaneously into the abdominal flanks of the recipient athymic mice. The growth of the tumors is monitored by measurement every 3 to 4 days by measuring the perpendicular diameters using a caliper. Tumor volumes are estimated using the formula 0.5 (width× width×length). The three different liposome formulations, at a dose of 3 mg doxorubicin/kg mouse body weight, are delivered as a boluswith a 25-gauge needle and 1 mL syringe into the tail vein of different groups of mice containing tumors on day 7 post tumor innoculation. Animals that receive the masked liposome containing the pH sensitive POD derivative exhibit a slower tumor growth rate than do animals that receive the other two formulations. This is because a greater fraction the doxorubicin dose enters the tumor from the targeted liposomes masked with the acid-cleavable PEG coating. Other ligands that are recognized by receptors that are present at both the disease target and some normal tissues at other locations in the body can also be beneficially masked by the POD ortho ester conjugate.

EXAMPLE 5

In another embodiment of the invention, a targeting ligand is attached via the pH sensitive linker so that the targeting ligand can be removed from the liposome, allowing the receptor to cycle back to the cell surface. Many cell surface receptors interact with their appropriate ligand, internalize with the ligand into the endosomal compartment and separate from the ligand due to the low pH of the endosomal compartment. The receptor then recycles to the cell surface and the internalized ligand stays within the cell. The receptor can then go through the process again. In targeted therapy there are a number of situations where the target receptor to which the drug carrier is directed is lost from the cell surface after interacting with the targeting ligand. This can occur if multiple receptors are cross-linked by the targeting ligands or it can occur if the steric bulk of the carrier does not permit the receptor to return to the cell surface. The consequence of this is that the number of drug molecules that can be delivered to the cell may be insufficient to cause a therapeutic effect. This can happen in the case of targeting of a drug carrier to a tumor where the number of receptors may already be low.

The methods of the invention allow the targeting ligand to be removed from the drug carrier after it has been internalized into the target cell. This can be done by attaching the targeting ligand to the head group of the LOC so that after the targeted liposome is internalized into the endosome the targeting ligand is removed from the liposome surface by the low pH found in this compartment. The receptor with the ligand is now able to recycle to the cell surface where the ligand is released and the receptor has another opportunity to interact with a targeted drug carrier. It can be appreciated that there are numerous types of receptors and their cognate ligands. These include peptides, proteins, carbohydrates, antibodies, and single chain antibodies that have been identified. Using the methods of this invention, these ligands can be attached to the encapsulator to target it to appropriate cells in the body for either a therapeutic or diagnostic purpose.

A 9-fluorenylmethoxycarbonyl aminopolyethylene glycol 3400-diortho ester-distearoyl glycerol conjugate can be prepared as generally described in Example 1 or 3 by replacing the methoxyPEG with a 9-fluorenylmethoxycarbonyl (FMOC) amino PEG 3400. The FMOC can be removed under basic conditions and the exposed amino group on the polyethylene glycol 3400-diortho ester-distearyl glycerol conjugate can be further modified to make an amine or sulfhydryl reactive pH sensitive lipid derivative by those skilled in the art. The derivative can then be attached to a targeting ligand such as transferrin under basic conditions (pH 9.0). This targeting ligand can then be incorporated into the liposome. When the liposome is exposed to acidic conditions such as found in the endosome the targeting ligand will be released from the liposome. This permits the transferrin receptor to recycle to the cell surface to undergo another round of internalization.

EXAMPLE 6

In yet another embodiment of the invention, the LOCs can be introduced into other encapsulators from micelle dispersions of the compound. Since the LOCs such as POD and DOC are pH-sensitive, it is advantageous to be able to insert the derivative into the drug carrier after all of the other processing steps have been completed. This permits the processing steps for the drug carrier to include acidification steps. This can be accomplished with the POD derivatives by dispersing the methoxypolyethylene glycol 2000-diortho ester-distearoyl glycerol conjugate (POD) in the appropriate alkaline buffer and then adding a suitable aliquot to a liposome preparation while maintaining the pH in the alkaline range.

In one example 10 $\mu$moles of methoxypolyethylene glycol 2000-diortho ester-distearoyl glycerol conjugate was dried from a chloroform solution unto the sides of a glass vessel. The dried film was rehydrated in 1 mL of 150 mM Tris/CL buffer pH 9.0 to create a 10 mM dispersion of POD. Under these conditions the POD has a Critical Micelle Concentration (CMC) of about 10 $\mu$M and micelles will be formed. An aliquot of 0.05 mL of the POD micelles is added to 1 mL of a 10 mM (total lipid) liposome suspension consisting of DSPC:Chol in the mole ratio of 55:40 in a 0.14 M NaCl-10 mM Tris, pH 8.0 buffer. The mixture is incubated at 37° C. for 2 hours. After this time the POD is incorporated into the liposome and the liposome can be injected into an animal.

EXAMPLE 7

In another method of the invention, LOCs from micelles can be incorporated into pre-formed separated DNA synthetic delivery systems. Cationic lipoplexes can be formed by mixing cationic liposomes with plasmid DNA as described in U.S. Pat. No. 5,972,600, which is hereby incorporated in its entirety by reference. Furthermore, cationic lipoplexes with a small diameter can be formed when DNA is added to sonicated cationic liposomes containing an excess molar ratio of positive charges over the negative charges contained on the nucleotide phosphates. Excess cationic liposomes can then be removed by separating the complexes from the excess liposomes. A difficulty with using these separated complexes to deliver genes in animals to sites other than the lung is that the positive charges on the complex avidly interact with the lung endothelial cells. Coating the complex with an amphipathic low-pH sensitive ortho ester conjugate of this invention prevents the lipoplex from binding to non-targeted cells in the body and in the long run enhance the deliver of the carried gene into the target cells. For example, the POD lipid can be used to coat the separated lipoplex. The coated lipoplex is then injected intravenously into animals and will circulate for a longer period relative to the non-coated lipoplex. When the coated lipoplex is taken up by the target cells into the endosomes the low pH causes the PEG to be cleaved from the POD and the exposed lipoplex can now transfect the cell.

In a specific example, cationic liposomes were prepared from N[1-,2dioleoyl-3-trimethyl]ammonium propane (DOTAP), and either dioleoylphosphatidyl-ethanolamine (DOPE) purchased from Avanti Polar Lipids (Alabaster, Ala.) or cholesterol, purchased from Sigma (St. Louis, Mo.). Liposomes were prepared by mixing the DOTAP lipid dissolved in chloroform with either cholesterol at a 5/4 molar ratio or DOPE at a 1:1 molar ratio, evaporated to dryness on a rotary evaporator and placed under high vacuum for at least 3 hrs. The lipid film was rehydrated with sterile filtered 5 mM HEPES (pH 7.4), vortexed briefly, and sonicated for 60 min under argon. Typical liposome-DNA complexes were prepared at room temperature by adding 500 $\mu$L of DNA containing 300 $\mu$g of the plasmid pCMV/IVS-luc$^+$ to 500 $\mu$L of liposome dispersion to create a final charge ratio of 10:1 (+/−charge ratio). The 1 mL volume containing the complexes were placed on a linear sucrose gradient as described in U.S. Pat. No. 5,972,600 and the complexes were separated from excess cationic liposomes. The hydrodynamic diameter of the liposomes (25 nm) and the separated complexes (70 nm) were determined with a dynamic laser light scattering apparatus (Coulter Electronics, Inc, Hialeah, Fla.). The final preparations contained about 250 $\mu$g of plasmid DNA in a volume of 1.0 mL 15% sucrose at a charge ratio of 3/1 (+/1). This represents a total lipid concentration of about 4.5 mM.

Ten $\mu$moles of methoxypolyethylene glycol 2000-diortho ester-distearoyl glycerol conjugate was dried from a chloroform solution unto the sides of a glass vessel. The dried film was rehydrated in 1 mL of 150 mM Tris/CL buffer pH 9.0 to create a 10 mM dispersion of POD. An aliquot of 0.025 mL of the POD micelles is added to 1 mL of the 4.5 mM (total lipid) lipoplex suspension consisting of DOTAP/Chol (5/4 molar ratio) or DOTAP/DOPE (1/1 molar ratio) in a 15% sucrose buffer. The mixture is incubated at 37° C. for 2 hours. After this time the POD is incorporated into the lipoplexes and the lipoplexes are injected into an animal via the tail vein. The POD coated lipoplexes are now able to deliver genes to the liver rather than to the lung.

EXAMPLE 8

In yet another method of the invention, LOCs are introduced from micelles into pre-formed amphotericin B encapsulator delivery systems. An amphotericin B cholesterol sulfate complex consisting of a 1:1 ratio of amphotericin B and cholesterol sulfate at a concentration of 10 mM cholesterol sulfate is dispersed in 5% dextrose. An aliquot of 0.05 mL of the POD micelles is added to 1 mL of the amphotericin B-cholesterol sulfate complex. The POD incorporates into the colloidal lipid system and provides a steric coating to inhibit the aggregation of this system in high ionic strength conditions such as found in the blood stream. Incorporation of the POD into complex increases the circulatory time after the intravenous administration into animals and permits the complex to distribute into the vicinity of abscesses caused by fungal infections. The pH in the vicinity of such microbial infections is slightly acidic. This causes the PEG to dissociate from the amphotericin B-cholesterol sulfate complex and permits the amphotericin B to transfer to fungi in the vicinity. Other amphotericin B lipidic formulations such as those formed from dimyristoylphosphatidylcholine and dimyristoylphosphatidylglycerol, those formed from phosphatidylserine cochleates, those formed from lipid emulsions, and those formed from other suitable encapsulators can be modified in a similar fashion to create amphotericin B delivery systems that circulate for a longer period after intravenous administration in animals then do the non-modified formulations.

EXAMPLE 9

In another embodiment of the invention, the LOCs can be incorporated from dried films into pre-formed liposomes, lipidic particles, or other suitable encapsulators. It is often desirable, due to the pH stability of the drug or to the process used to prepare the lipidic delivery system, to incorporate the pH sensitive lipid from a dry form into the lipidic drug carrier formulation in suspension prior to its use. This can be accomplished using the LOCs of the invention. For example, methoxypolyethylene glycol 2000-diortho ester-distearoyl glycerol conjugate (POD) is dried onto the sides of a glass vessel or container from an organic solvent such as methylene chloride to form a dry POD film. As a dry film the pH sensitive derivative is stable for a prolonged period. The encapsulator system that is to be modified is then added in suspension to the dried film. The molar ratio of the total lipids added to the dry film to the dried POD is usually in the vicinity of 20 total lipids to 1 POD lipid. The mixture is allowed to incubate for a period of 1–3 hours, usually two hours at 37° C. and the POD will then spontaneously transfer from the dry film into the encapsulator delivery system. The optimal conditions for this transfer will be at a pH greater than 7.0 in a predominantly aqueous system. However one skilled in the art will recognize that adjustments can be made if non-aqueous solutions or mixtures of solvents such as ethanol/water are used to mix the preformed lipidic delivery system with the dry POD film. In this manner the shelf life of the pH sensitive lipid derivative can be significantly extended and the modified formulation can be extemporaneously prepared at the site to provide the drug carrier.

EXAMPLE 10

In yet another embodiment of the invention, the amphipathic low pH sensitive compounds can introduced into other encapsulators from non-aqueous but water-miscible solvents. Since the amphipathic low pH sensitive compounds such as POD and DOC are pH sensitive, it is advantageous to be able to insert the derivative into the drug carrier after all of the other processing steps have been completed. This permits the processing steps for the drug carrier to include acidification steps. This can be accomplished with the POD derivatives by dispersing the methoxypolyethylene glycol 2000-diortho ester-distearoyl glycerol conjugate (POD) in an appropriate non-aqueous solvent such as acetonitrile, dimethylsulfoxide, glyme, methylpyrolidone, ethanol, triacetin or mixtures thereof.

In one example 10 μmoles of polyethylene glycol 2000-diortho ester-distearoyl glycerol conjugate was dissolved in glyme. An aliquot of 0.05 mL of the glyme solution of POD is added to 1 mL of a 10 mM (total lipid) liposome suspension consisting of DSPC:Chol in the mole ratio of 55:40 in a 0.14 M NaCl-10 mM Tris, pH 8.0 buffer. The mixture is incubated at 37° C. for 10 minutes. After this time the POD is incorporated into the liposome and the liposome can be injected into an animal.

EXAMPLE 11

Figure 22:
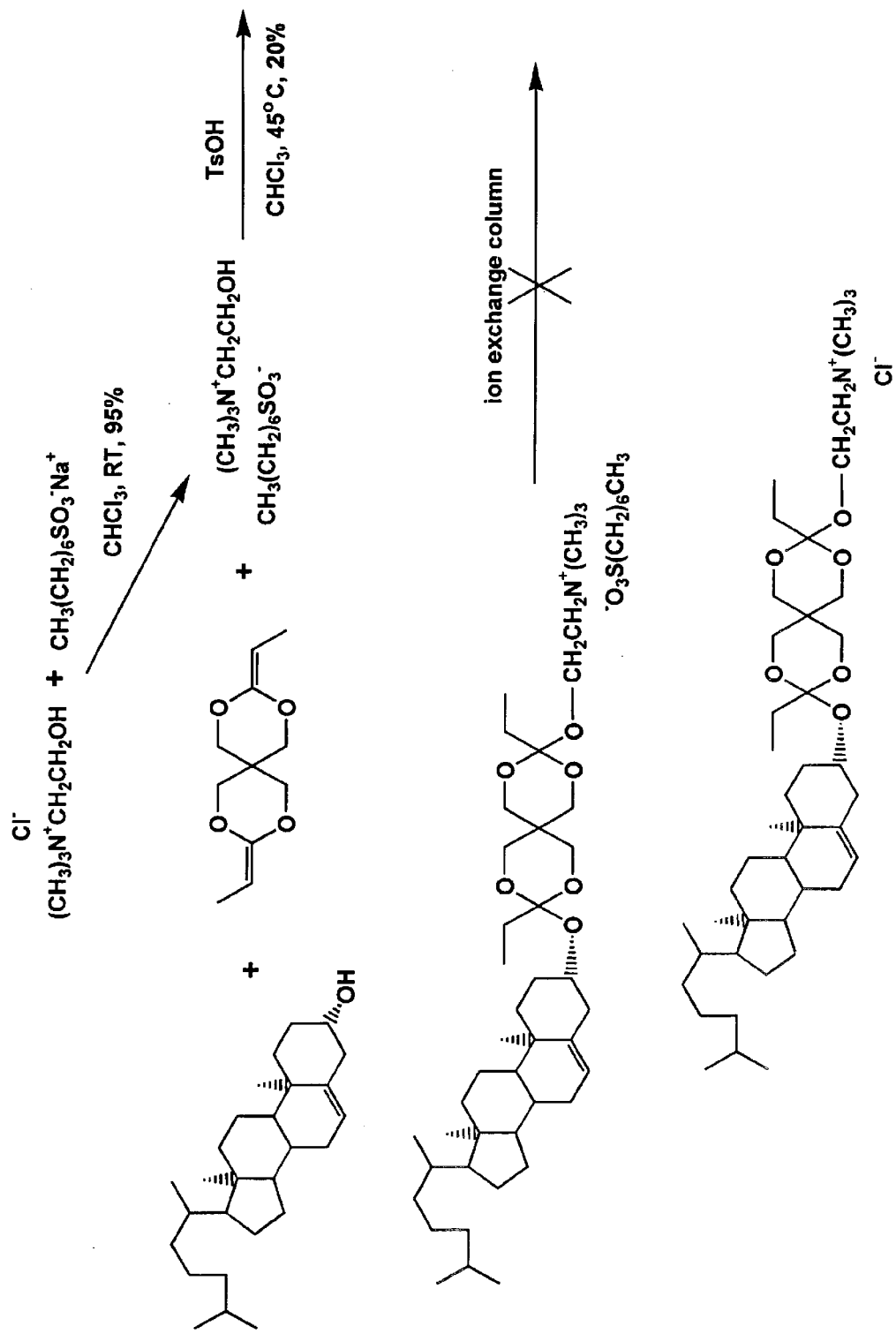
FIG. 22 shows the synthesis of yet other alternative embodiments of LOCs of the invention.

As an alternative to the compositions disclosed above in Example 1, diketene acetal ortho ester derivatives can be used to link hydrophobic groups such as cholesterol or tocopherol to the hydrophilic portions of the invention as shown in FIG. 22. The orthoester conjugates in these embodiments are prepared using a similar protocol to POD. The commercially available chloride salt of choline needs to be converted to the more hydrophobic heptanesulfonate salt to increase its solubility in chloroform. The heptanesulfonate salt of choline can be prepared by mixing the commercially available choline chloride with one equivalent of sodium heptanesulfonate following by stirring in chloroform at room temperature for 5 hours. The chloroform suspension is then filtered and the filtrate evaporated to yield choline heptanesulfonate producing a 95% synthetic yield. Thus, PEG or another suitable hydrophilic head group can be attached to either cholesterol or tocopherol by this reaction sequence. The nature of the hydrophobic derivative can be selected to provide the appropriate retention of the modified orthoester in the lipidic body. For instance, acyl chain lengths other than C18 can be used in the diacylglycerol portion of the derivative.

Described herein is a preferred embodiment, however, one skilled in the art that pertains to the present invention will understand that there are equivalent

What is claimed is:

1. A composition having an amphipathic characteristic comprising a hydrophilic portion and a hydrophobic portion joined by an ortho ester linker, wherein the ortho ester linker hydrolyzes at an increasing rate as the pH is reduced below 7, wherein cleavage of the ortho ester linker directly detaches the hydrophobic portion and eliminates the amphipathic characteristic, wherein the hydrophilic portion is selected from the group consisting of methoxypolyethylene, polyethyleneglycol, hydroxylated dendrons, poly(methyloxazoline), poly(ethyloxazoline) and polyvinylpyrolidone and wherein the hydrophobic group is selected from the group consisting of diacyl glycerols, distearoylglycerol, dipalmitoylglycerol, dimyristoyl glycerol, dioleoyl glycerol, tocopherol, cholesterol, coenzyme Q, and ceramide.

2. The composition of claim 1, wherein the hydrophilic portion comprises a polymer capable of increasing circulation time in the bloodstream of animals when incorporated on the surface of an encapsulator.

3. The composition of claim 2, wherein the hydrophilic portion comprises polyethyleneglycol having a molecular weight from 200 to 20000.

4. A composition comprising an encapsulator selected from the group consisting of liposomes, emulsions, micelles and lipidic bodies, wherein the encapsulator comprises a conjugate having an amphipathic characteristic with a hydrophilic portion and a hydrophobic portion capable of anchoring the conjugate to the encapsulator, wherein the hydrophilic portion and the hydrophobic portion are joined by an ortho ester linker, wherein the ortho ester linker hydrolyzes and cleaves at an increasing rate as the pH is reduced below 7 and wherein cleavage of the ortho ester directly detaches the hydrophilic portion from the hydrophobic portion and the encapsulator, eliminates the amphipathic characteristic and destabilizes the encapsulator.

5. The composition of claim 4, wherein the hydrophilic portion comprises a targeting ligand.

6. The composition of claim 4, wherein the hydrophilic portion comprises a cationic group.

7. The composition of claim 1, wherein the hydrophobic portion is selected from the group consisting of tocopherol, cholesterol, coenzyme Q, and ceramide.

8. The composition of claim 1, wherein the ortho ester linker comprises a diortho ester.

9. The composition of claim 8, wherein the ortho ester linker comprises a diketene acetal group.

10. The composition of claim 8, wherein the ortho ester linker comprises a 3,9-dialkoxylated 3,9-Diethyl-2,4,8,10-tetraoxaspiro[5,5] undecane derivative.

11. The composition of claim 8, wherein the composition comprises 3,9-Diethyl-3-(2,3-distearoyloxypropyloxy)-9-(methoxypolyethyleneglycol2000-1-yl)-2,4,8,10-tetraoxaspiro[5,5]undecane.

12. The composition of claim 4, wherein the ortho ester linker comprises a single ortho ester.

13. The composition of claim 12, wherein the ortho ester linker comprises a dichloromethylmethyl ether and the hydrophilic portion is cationic.

14. The composition of claim 13, wherein the composition comprises N,N-dimethyl-(4-methoxy-(cholest-5-en-3β-oxy)hept-3,5-dioxa-yl)ammonium (DOC).

15. The composition of claim 13, wherein the composition comprises N,N-trimethyl-(4-methoxy-(cholest-5-en-3β-oxy)hept-3,5-dioxa-yl)amine iodide.

16. The composition of claim 4, wherein the encapsulator further comprises a lipid.

17. The composition of claim 16, wherein the lipid comprises DOPE.

18. The composition of claim 17, comprising DOPE/methoxypolyethylene glycol 2000-diortho ester-distearoyl glycerol conjugate (POD) in a ratio of about 97:3 to 85:15.

19. The composition of claim 17, comprising DOPE/dimethylethanolamine-ortho ester-cholesterol (DOC).

20. The composition of claim 18, wherein the lipid comprises a fusogenic lipid.

21. The composition of claim 16, wherein the lipid comprises a lipid selected form the group consisting of phosphatidylcholine, phosphatidylglycerol, phosphatidylethanolamine, phosphatidylserine, phosphatidic acid, cholesteryl hemisuccinate, cholesterol sulfate, ceramide, cardiolipid, N[1-,2dioleoyl-3-trimethyl] ammonium propane (DOTAP), dimethyldioctadecylammonium bromide (DDAB), 1-palmitoyl-2-oleoyl-sn-glycero-3-ethyl-phosphocholine,N[1-(2,3-dioleyloxy)propyl]-N,N,N,-triethylammonium (DOTMA),triglycerides, squalene, coenzyme Q and alkyl acylcamitine esters.

22. The composition of claim 16, wherein the lipid further comprises a targeting ligand.

23. The composition of claim 22, wherein the targeting ligand is selected a group consisting of hyaluronan, antibodies, peptides, folate, receptor antagonists, carbohydrates, transferrin, protein hormones, and cytokines.

24. The composition of claim 4, wherein the hydrophilic portion comprises a targeting ligand.

25. The composition of claim 24, wherein the targeting ligand is selected a group consisting of hyaluronan, antibodies, peptides, folate, receptor antagonists, carbohydrates, transferrin, protein hormones, and cytokines.

26. An encapsulator for delivering a compound, comprising a low pH sensitive lipidic composition having an amphipathic characteristic and comprising an ortho ester linker wherein the encapsulator exhibits degradation of less than 10% within 3 hours at a pH of 7.4 and degradation greater than 50% within 60 minutes at a pH of 5.0, wherein the encapsulator is selected from the group consisting of liposomes, emulsions, micelles and lipidic bodies and wherein hydrolysis and cleavage of the ortho ester linker directly detaches a hydrophilic portion of the lipidic composition from a hydrophobic portion of the lipidic composition and the encapsulator to eliminate the amphipathic characteristic and destabilize the encapsulator.

27. The encapsulator of claim 26, wherein the amphipathic low-pH sensitive lipidic composition comprises a hydrophilic portion, a hydrophobic portion and an ortho ester linker.

28. The encapsulator of claim 27, wherein the hydrophilic portion comprises PEG.

29. The encapsulator of claim 28, wherein the ortho ester linker comprises a diortho ester.

30. The encapsulator of claim 26, further comprising a lipid.

31. The encapsulator of claim 26, wherein the lipid is selected from the group consisting of phosphatidylcholine, phosphatidylglycerol, phosphatidylethanolamine, phosphatidylserine, phosphatidic acid, cholesteryl hemisuccinate, cholesterol sulfate, ceramide, cardiolipid, N[1-,2dioleoyl-3-trimethyl]ammonium propane (DOTAP), dimethyldioctadecylammonium bromide (DDAB), 1-palmitoyl-2-oleoyl-sn-glycero-3-ethyl-phosphocholine,N[1-(2,3-dioleyloxy)propyl]-N,N,N,-triethylammonium (DOTMA), triglycerides, squalene, coenzyme Q and alkyl acylcarnitine esters, and dioleoylphosphatidyl ethanolamine (DOPE).

32. The encapsulator of claim 29, wherein the hydrophilic portion comprises PEG, further comprising a lipid.

33. The encapsulator of claim 26, wherein the ortho ester linker comprises a dialkoxy methoxy methine group.

34. A method for delivering a drug to a cell comprising the steps of providing an encapsulator comprising a lipidic ortho ester conjugate (LOC) having an amphipathic characteristic and the drug, wherein the encapsulator is selected from the group consisting of liposomes, emulsions, micelles and lipidic bodies, wherein hydrolysis and cleavage of an ortho ester linker directly detaches a hydrophilic portion of the lipidic ortho ester conjugate from a hydrophobic portion of the lipidic ortho ester conjugate and the encapsulator to eliminate the amphipathic characteristic and destabilize the encapsulator and administering the encapsulator.

35. The method of claim 34, further comprising the steps of exposing the encapsulator to reduced pH, degrading the encapsulator and releasing the drug.

36. The method of claim 34, further comprising the steps of preparing a dry powder formulation of the encapsulator and administering the dry powder.

37. The method of claim 36, further comprising the steps of preparing a dry powder formulation of the encapsulator, rehydrating the encapsulator in an appropriate buffer and administering the encapsulator.

38. A method for incorporating a lipidic ortho ester conjugate (LOC) having an amphipathic characteristic into an encapsulator, the lipidic ortho ester conjugate comprising an ortho ester linker wherein hydrolysis and cleavage of the ortho ester linker directly detaches a hydrophilic portion of the lipidic ortho ester conjugate from a hydrophobic portion of the lipidic ortho ester conjugate and the encapsulator to eliminate the amphipathic characteristic and destabilize the encapsulator, comprising the step of mixing the encapsulator with the lipidic ortho ester conjugate (LOC).

39. The method of claim 38, further comprising the steps of:
a) preparing a dry film of the lipidic ortho ester conjugate (LOC);
b) rehydrating the a lipidic ortho ester conjugate (LOC) to form micelles; and
c) combining the micelles with an encapsulator suspension.

40. The method of claim 38, wherein the encapsulator comprises a cationic lipoplex further comprising the steps of preparing a cationic lipoplex and coating the lipoplex with the lipidic ortho ester conjugate (LOC).

41. The method of claim 38 further comprising the steps of:
a) preparing a dry film of the lipidic ortho ester conjugates (LOC);
b) preparing an encapsulator suspension; and
c) combining the encapsulator suspension with the dry film.

42. The method of claim 38, further comprising the steps of:
a) preparing the lipidic ortho ester conjugate (LOC) in a non-aqueous, water miscible solvent b) preparing an encapsulator suspension; and c) combining the encapsulator suspension with the lipidic ortho ester conjugate (LOC) in the water miscible solvent.

43. The method of claim 42, wherein the non-aqueous, water miscible solvent is selected from the group consisting of acetonitrile, dimethylsulfoxide, glyme, methylpyrrolidone, ethanol, triacetin and mixtures of these.

44. A method for storing an encapsulator for delivering a compound, comprising the steps of:
a) providing an encapsulator comprising a low pH sensitive lipidic compound comprising an amphipathic characteristic and an ortho ester linker wherein the encapsulator exhibits degradation of less than 10% within 3 hours at a pH of 7.4 and degradation greater than 50% within 60 minutes at a pH of 5.0 and wherein hydrolysis and cleavage of the ortho ester linker directly detaches a hydrophilic portion of the lipidic ortho ester conjugate from a hydrophobic portion of the lipidic ortho ester conjugate and the encapsulator to eliminate the amphipathic characteristic and destabilize the encapsulator; and
b) lyophilizing the encapsulator.

45. The method of claim 44, further comprising the step of milling the lyophilized encapsulator to form a dry powder.

46. A method for gene transfer comprising the steps of:
a) providing an encapsulator comprising a low pH sensitive lipidic composition having an amphipathic characteristic, an acid labile orthoester bond and a polynucleotide, wherein the encapsulator exhibits degradation of less than 10% within 3 hours at a pH of 7.4 and degradation greater than 50% within 60 minutes at a pH of 5.0, and wherein hydrolysis and cleavage of the orthoester bond directly detaches a hydrophilic portion of the lipidic composition from a hydrophobic portion of the lipidic composition and the encapsulator to eliminate the amphipathic characteristic and destabilize the encapsulator;
b) administering the encapsulator to an animal;
c) exposing the encapsulator to a reduced pH to degrade the encapsulator; and
d) releasing the polynucleotide.

47. The method of claim 46, further comprising the step of forming a dry powder formulation from the encapsulator prior to administering the encapsulator.

48. The method of claim 47, further comprising the step of rehydrating the encapsulator prior to administering the encapsulator.

* * * * *

UNITED STATES PATENT AND TRADEMARK OFFICE
CERTIFICATE OF CORRECTION

PATENT NO. : 6,897,196 B1
DATED : May 24, 2005
INVENTOR(S) : Francis C. Szoka, Jr. and Xin Guo It is certified that error appears in the above-identified patent and that said Letters Patent is hereby corrected as shown below:

Column 1,
Line 17, please insert the following:
-- This invention was made with Government support under Grant No. DK46052, awarded by the National Institutes of Health. The Government has certain rights in this invention. --.

Signed and Sealed this

First Day of November, 2005

JON W. DUDAS
*Director of the United States Patent and Trademark Office*